(12) United States Patent

Heo et al.

(10) Patent No.: US 12,564,380 B2

(45) Date of Patent: Mar. 3, 2026

(54) WIRELESS PROBE

(71) Applicant: Samsung Medison Co., Ltd., Hongcheon-gun (KR)

(72) Inventors: Minho Heo, Seoul (KR); Sokjae Shin, Seoul (KR); Hyungwon Yoon, Seoul (KR); Yonghyun Kim, Seoul (KR); Jungmin Kim, Seoul (KR); Jaehan Jeon, Seoul (KR); Yongkwan Kim, Seoul (KR)

(73) Assignee: SAMSUNG MEDISON CO., LTD., Hongcheon-Gun (KR)

( * ) Notice: Subject to any disclaimer, the term of this patent is extended or adjusted under 35 U.S.C. 154(b) by 0 days.

(21) Appl. No.: 18/600,259

(22) Filed: Mar. 8, 2024

(65) Prior Publication Data

US 2024/0315669 A1 Sep. 26, 2024

(30) Foreign Application Priority Data

Mar. 22, 2023 (KR) ........................ 10-2023-0037596
Aug. 23, 2023 (KR) ........................ 10-2023-0110768

(51) Int. Cl.
*A61B 8/00* (2006.01)
*G01S 7/52* (2006.01)

(52) U.S. Cl.
CPC .......... *A61B 8/4472* (2013.01); *A61B 8/4477* (2013.01); *G01S 7/52079* (2013.01)

(58) Field of Classification Search
CPC ... A61B 8/4472; A61B 8/4477; A61B 8/4494; A61B 8/56; A61B 8/4444; G01S 7/52079
See application file for complete search history.

(56) References Cited

U.S. PATENT DOCUMENTS

| | | | |
|---|---|---|---|
| 6,120,452 A | 9/2000 | Barthe et al. | |
| 9,532,768 B2 | 1/2017 | Marteau et al. | |
| 2008/0194961 A1* | 8/2008 | Randall .............. | G01S 7/52017 |
| | | | 600/459 |
| 2010/0168576 A1* | 7/2010 | Poland .................. | G01S 7/5208 |
| | | | 600/443 |

(Continued)

FOREIGN PATENT DOCUMENTS

| | | |
|---|---|---|
| CN | 101366662 A | 2/2009 |
| CN | 109893170 A | 6/2019 |

(Continued)

OTHER PUBLICATIONS

The Extended European Search Report dated Jul. 15, 2024 issued in European Patent Application No. 24152322.4.

(Continued)

*Primary Examiner* — Kaitlyn E Sebastian
(74) *Attorney, Agent, or Firm* — Morgan Lewis & Bockius LLP

(57) ABSTRACT

A wireless probe includes a housing having a length in a first direction, a first transducer located at one end of the housing in the first direction, a circuit board located inside the housing and electrically connected to the first transducer, and a battery located between the first transducer and the circuit board inside the housing and having a length in a second direction perpendicular to the first direction, wherein the housing is configured to allow the battery to be inserted and separated along the second direction.

15 Claims, 32 Drawing Sheets

(56)         References Cited

U.S. PATENT DOCUMENTS

| | | | |
|---|---|---|---|
| 2010/0286527 A1* | 11/2010 | Cannon | A61B 8/42 |
| | | | 600/459 |
| 2013/0143080 A1* | 6/2013 | Byun | H01M 50/528 |
| | | | 429/61 |
| 2018/0140276 A1 | 5/2018 | Cai et al. | |
| 2021/0137495 A1* | 5/2021 | Noguchi | A61B 8/4455 |
| 2022/0304658 A1 | 9/2022 | Sene | |

FOREIGN PATENT DOCUMENTS

| | | | |
|---|---|---|---|
| EP | 3960090 A1 | | 3/2022 |
| JP | 2006343261 A | * | 12/2006 |
| JP | 2022-164871 A | | 10/2022 |
| KR | 10-2022-0157249 A | | 11/2022 |

OTHER PUBLICATIONS

European Communication dated Jul. 3, 2025 issued in European Patent Application No. 24152322.4.

* cited by examiner

FIG. 1

WIRELESS PROBE

CROSS-REFERENCE TO RELATED APPLICATION

This application is based on and claims priority under 35 U.S.C. § 119 to Korean Patent Application Nos. 10-2023-00037596 and 10-2023-0110768, respectively filed on Mar. 22, 2023 and Aug. 23, 2023, in the Korean Intellectual Property Office, the disclosures of which are incorporated by reference herein in their entirety.

BACKGROUND

1. Field

The disclosure provides a wireless probe including a battery that may be separated and assembled.

2. Description of the Related Art

An ultrasound diagnostic apparatus irradiates an ultrasound signal generated from a transducer of a probe to an object, receives information from a signal reflected from the object, and obtains at least one image of a region (e.g., soft tissue or blood flow) inside the object.

In such an ultrasound diagnostic apparatus, a wireless probe connected to an external device, for example, a main body, through a wireless network is being developed so that a user may operate the probe without spatial constraints. The wireless probe does not include a separate wiring for receiving power from the outside, and may receive power by using an internal battery.

However, because such a wireless probe receives power by using a battery, the battery needs to be charged or replaced with a new battery before becoming completely discharged.

SUMMARY

A wireless probe according to an embodiment may provide a structure in which a battery may be separated and assembled to be located between a transducer and a circuit board.

A wireless probe according to an embodiment may allow a battery to be inserted into a housing along a longitudinal direction of the battery, thereby facilitating separation and assembly of the battery and improving waterproof performance.

Additional aspects will be set forth in part in the description which follows and, in part, will be apparent from the description, or may be learned by practice of the presented embodiments.

According to an aspect of the disclosure, a wireless probe includes a housing having a length in a first direction, a first transducer located at one end of the housing in the first direction, a circuit board located inside the housing and electrically connected to the first transducer, and a battery located between the first transducer and the circuit board inside the housing and having a length in a second direction perpendicular to the first direction, wherein the housing is configured to allow the battery to be inserted and separated along the second direction.

The housing may include an outer housing forming an exterior and including an opening formed at one end in the second direction, a housing cap forming an exterior and configured to open and close the opening, and a battery accommodating unit located inside the outer housing and accommodating the battery inserted through the opening therein.

The battery accommodating unit may be connected to the opening, has a cross-sectional shape corresponding to a cross-sectional shape of the battery, and extends along the second direction.

The wireless probe may further include at least one flexible circuit unit electrically connecting the circuit board to the first transducer and formed to bypass the battery accommodating unit.

The battery may include a first electrode portion and a second electrode portion located adjacent to each other at the front in an insertion direction.

The battery may include a battery body including a first electrode and a second electrode having different polarities and provided at both ends in a longitudinal direction, and an electrode adjusting assembly exposing the first electrode to outside to form the first electrode portion, covering the second electrode, and electrically connected to the second electrode to form the second electrode portion adjacent to the first electrode portion.

The electrode adjusting assembly may include an inner insulator configured to surround an outer surface of the battery body and expose the first electrode and the second electrode through both ends of the inner insulator, an electrode moving body including an electrode contact portion contacting the second electrode exposed through the inner insulator, the second electrode portion located at a position spaced apart from the electrode contact portion, and an extending portion electrically connecting the electrode contact portion to the second electrode portion, and an outer insulator configured to surround an outer surface of the inner insulator, cover the electrode contact portion and the extending portion of the electrode moving body, and expose the second electrode portion.

The battery accommodating unit may include a first electrode terminal for electrical contact with the first electrode portion of the battery, and a second electrode terminal for electrical contact with the second electrode portion of the battery, wherein directions of the first electrode terminal and the second electrode terminal are perpendicular to each other.

An outer diameter of the second electrode portion may be less than an outer diameter of the outer insulator so that the second electrode portion forms a concave portion of the battery.

When the battery is inserted into the battery accommodating unit, a distance between the second electrode portion and the opening along the second direction may be greater than a distance between the second electrode and the opening along the second direction.

A difference between a length of the first transducer along the second direction and a length of the battery along the second direction may be 20% or less of the length of the battery along the second direction.

The housing cap may have an open position for opening the opening and a closed position for closing the opening, wherein the housing cap includes a locking member configured to maintain the closed position.

The wireless probe may further include a manipulation member configured to facilitate release of a locked state by the locking member.

The wireless probe may further include a sealing member located on at least one of the outer housing and the housing cap to prevent penetration of water between the outer housing and the housing cap.

The wireless probe may further include a sensor configured to detect whether the housing cap is at an open position, wherein an operation of the first transducer is controlled based on a detection result of the sensor.

The wireless probe may further include a second transducer located at the other end of the housing, wherein a width of the first transducer in the second direction is different from a width of the second transducer in the second direction.

BRIEF DESCRIPTION OF THE DRAWINGS

The above and other aspects, features, and advantages of certain embodiments will be more apparent from the following description taken in conjunction with the accompanying drawings, in which:

FIG. 1 is a block diagram illustrating a configuration of an ultrasound diagnostic apparatus, according to an embodiment;

DETAILED DESCRIPTION

Figure 2:
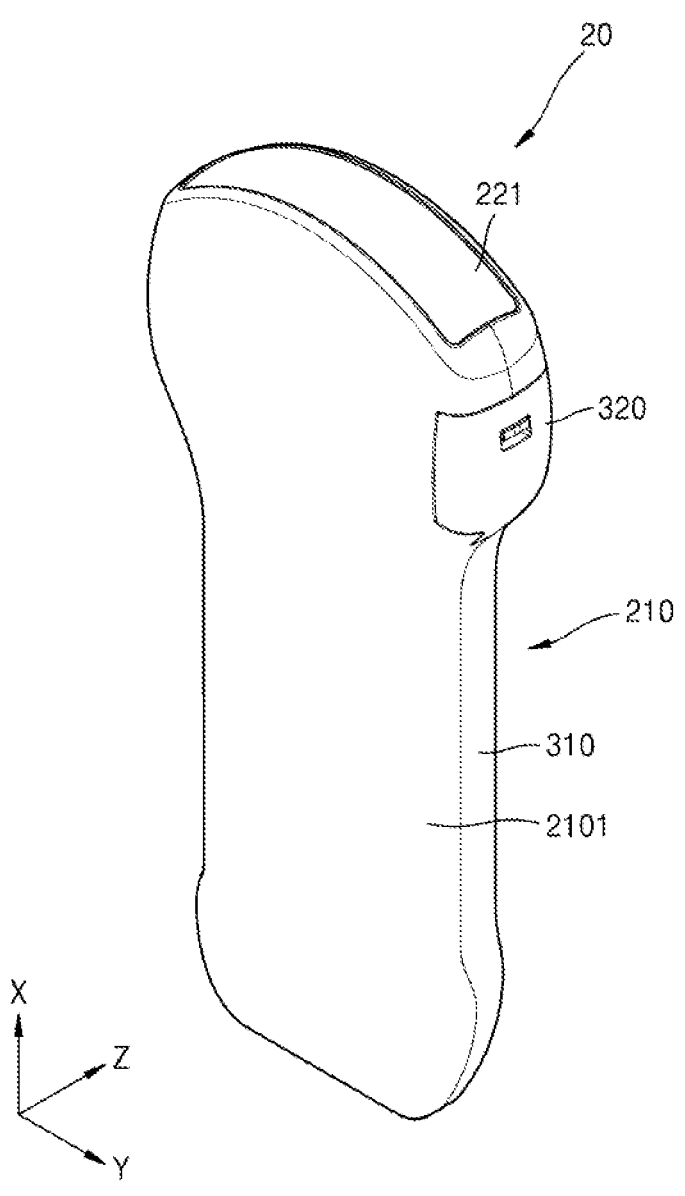
FIG. 2 is a perspective view illustrating a wireless probe, according to an embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Hereinafter, principles and embodiments will be described in detail in order to fully convey the scope of the claims of the disclosure and enable one of ordinary skill in the art to embody and practice the disclosure. The embodiments may be implemented in various forms.

Throughout the disclosure, like reference numerals denote like elements. All elements of the embodiments are not described in the disclosure, and descriptions of matters well known in the art to which the disclosure pertains or repeated descriptions between embodiments will not be given. The terms such as "module", "part", and "portion" used herein denote those that may be embodied by software or hardware. According to embodiments, a plurality of modules, parts, or portions may be embodied by a single unit or element, or a single part or portion may include a plurality of elements. Embodiments and principles of the embodiments will now be described with reference to the accompanying drawings.

In the disclosure, an image may include a medical image obtained by a medical imaging apparatus such as magnetic resonance imaging (MRI) apparatus, a computed tomography (CT) apparatus, an ultrasound imaging apparatus, or an X-ray imaging apparatus.

In the disclosure, an "object" may be a target to be imaged and may include a human, an animal, or a part of a human or animal. For example, an object may include a body part (e.g., an organ) or a phantom.

Throughout the disclosure, an "ultrasound image" refers to an image of an object processed based on an ultrasound signal transmitted to the object and reflected therefrom.

Hereinafter, embodiments will be described in detail with reference to the drawings.

Figure 1:
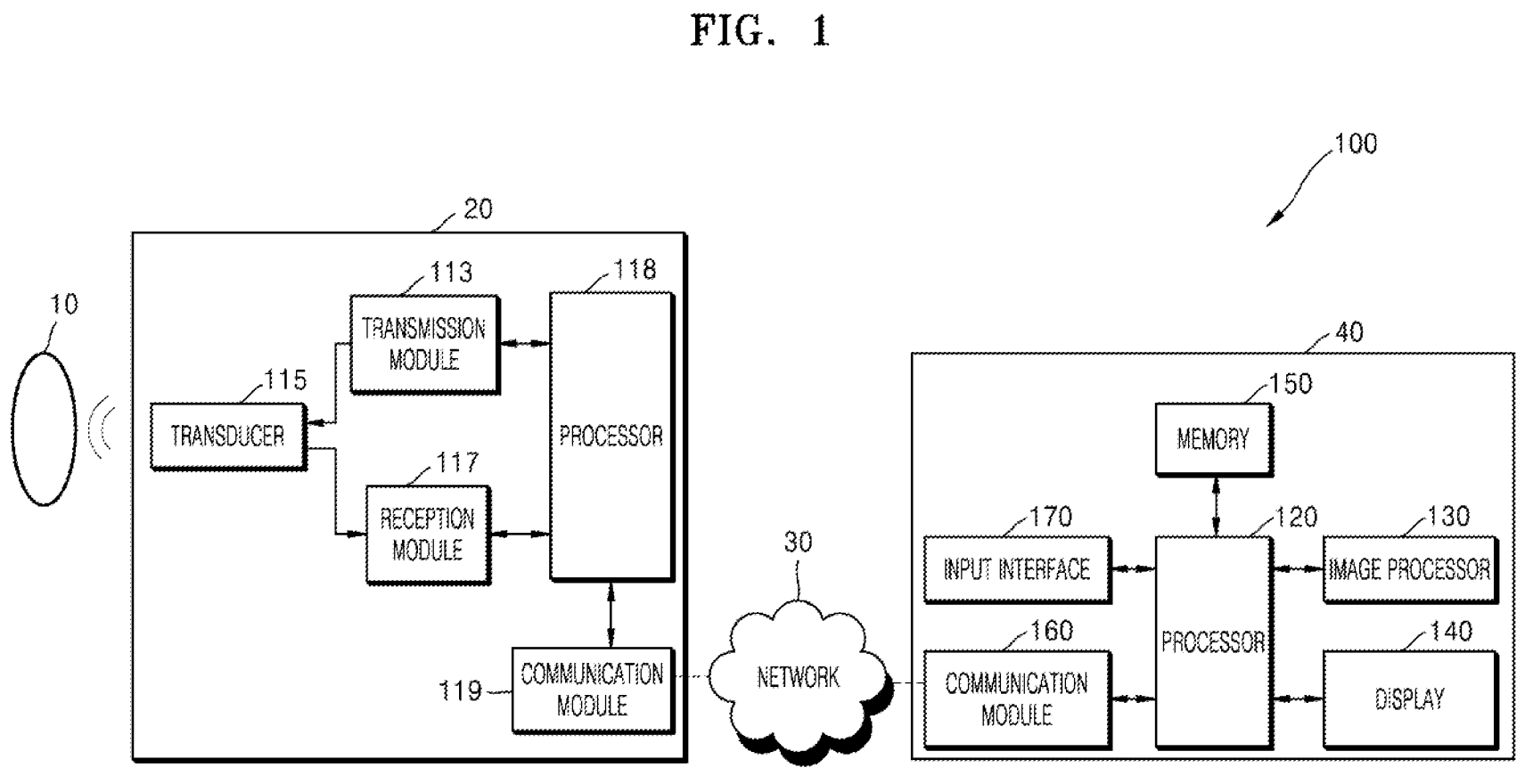

FIG. 1 is a block diagram illustrating a configuration of an ultrasound diagnostic apparatus 100, according to an embodiment.

Referring to FIG. 1, the ultrasound diagnostic apparatus 100 may include a wireless probe 20 and an ultrasound imaging apparatus 40.

The wireless probe 20 may include a transmission module 113, a transducer 115, a reception module 117, a processor 118, and a communication module 119. Although the wireless probe 20 includes both the transmission module 113 and the reception module 117 in FIG. 1, according to an implementation type, the wireless probe 20 may include only some of components of the transmission module 113 and the reception module 117 and some of components of the transmission module 113 and the reception module 117 may be included in the ultrasound imaging apparatus 40. Alternatively, the wireless probe 20 may further include an image processor 130.

The transducer 115 may include a plurality of transducer members. The plurality of transducer members may transmit an ultrasound signal to an object 10 according to a transmission signal applied from the transmission module 113. The plurality of transducer members may receive an ultrasound signal reflected from the object 10 to form a reception signal.

The processor 118 controls the transmission module 113 to form a transmission signal to be applied to each of the plurality of transducer members, by considering positions and focal points of the plurality of transducer members.

The processor 118 controls the reception module 117 to convert a reception signal received from the transducer 115 through analog-to-digital conversion and add digitally converted reception signals by considering positions and focal points of the plurality of transducer members to generate ultrasound data. Alternatively, when the wireless probe 20 includes the image processor 130, an ultrasound image may be generated by using the generated ultrasound data.

The communication module 119 may wirelessly transmit the generated ultrasound data or ultrasound image to the ultrasound imaging apparatus 40 through a wireless network. Also, the communication module 119 may receive a control signal and data from the ultrasound imaging apparatus 40.

Also, the ultrasound diagnostic apparatus 100 may be connected to one or more wireless probes 20 according to an implementation type.

The ultrasound imaging apparatus 40 may receive the ultrasound data or ultrasound image from the wireless probe 20. The ultrasound imaging apparatus 40 may include a processor 120, the image processor 130, a display 140, a memory 150, a communication module 160, and an input interface 170.

The image processor 130 generates an ultrasound image, by using the ultrasound data received from the wireless probe 20.

The display 140 may display the ultrasound image received from the wireless probe 20, the ultrasound image generated by the ultrasound imaging apparatus 40, and various information processed by the ultrasound diagnostic apparatus 100. The ultrasound diagnostic apparatus 100 may include one or more displays 140 according to an implementation type. Also, the display 140 may include a touch panel or a touchscreen.

The processor 120 may control an overall operation of the ultrasound diagnostic apparatus 100 and a signal flow between internal elements of the ultrasound diagnostic apparatus 100. The processor 120 may perform or control various operations or functions of the ultrasound diagnostic apparatus 100 by executing a program stored in the memory 150. Also, the processor 120 may control an operation of the ultrasound diagnostic apparatus 100 by receiving a control signal from the input interface 170 or an external device.

The ultrasound imaging apparatus 40 includes the communication module 160, and may be connected to an external device (e.g., a server, a medical device, a portable device (e.g., a smartphone, a tablet PC, or a wearable device)) through the communication module 160.

The communication module 160 may include one or more elements that enable communication with an external device. For example, the communication module 160 may include at least one of a short-range communication module, a wired communication module, and a wireless communication module.

The communication module 160 may receive a control signal and data from an external device and transmit the received control signal to the processor 120 so that the processor 120 controls the ultrasound diagnostic apparatus 100 according to the received control signal.

Alternatively, the processor 120 may transmit a control signal to an external device through the communication module 160, to control the external device according to the control signal of the processor.

For example, the external device may process data of the external device according to the control signal of the processor received through the communication module.

Because a program for controlling the ultrasound diagnostic apparatus 100 may be installed in the external device, the program may include instructions for performing some or all of operations of the processor 120.

The program may be pre-installed in the external device, or a user of the external device may download and install the program from a server that provides an application. A recording medium in which the program is stored may be included in the server that provides the application.

The memory 150 may store various data or programs for driving and controlling the ultrasound diagnostic apparatus 100, input/output ultrasound data, and an ultrasound image.

The input interface 170 receives the user's input for controlling the ultrasound diagnostic apparatus 100. For example, the user's input may include, but is not limited to, an input manipulating a button, a keypad, a mouse, a trackball, a jog switch, or a knop, an input that touches the touch pad or the touchscreen, a voice input, a motion input, or a biometric information input (e.g., iris recognition or fingerprint recognition).

Figure 3:
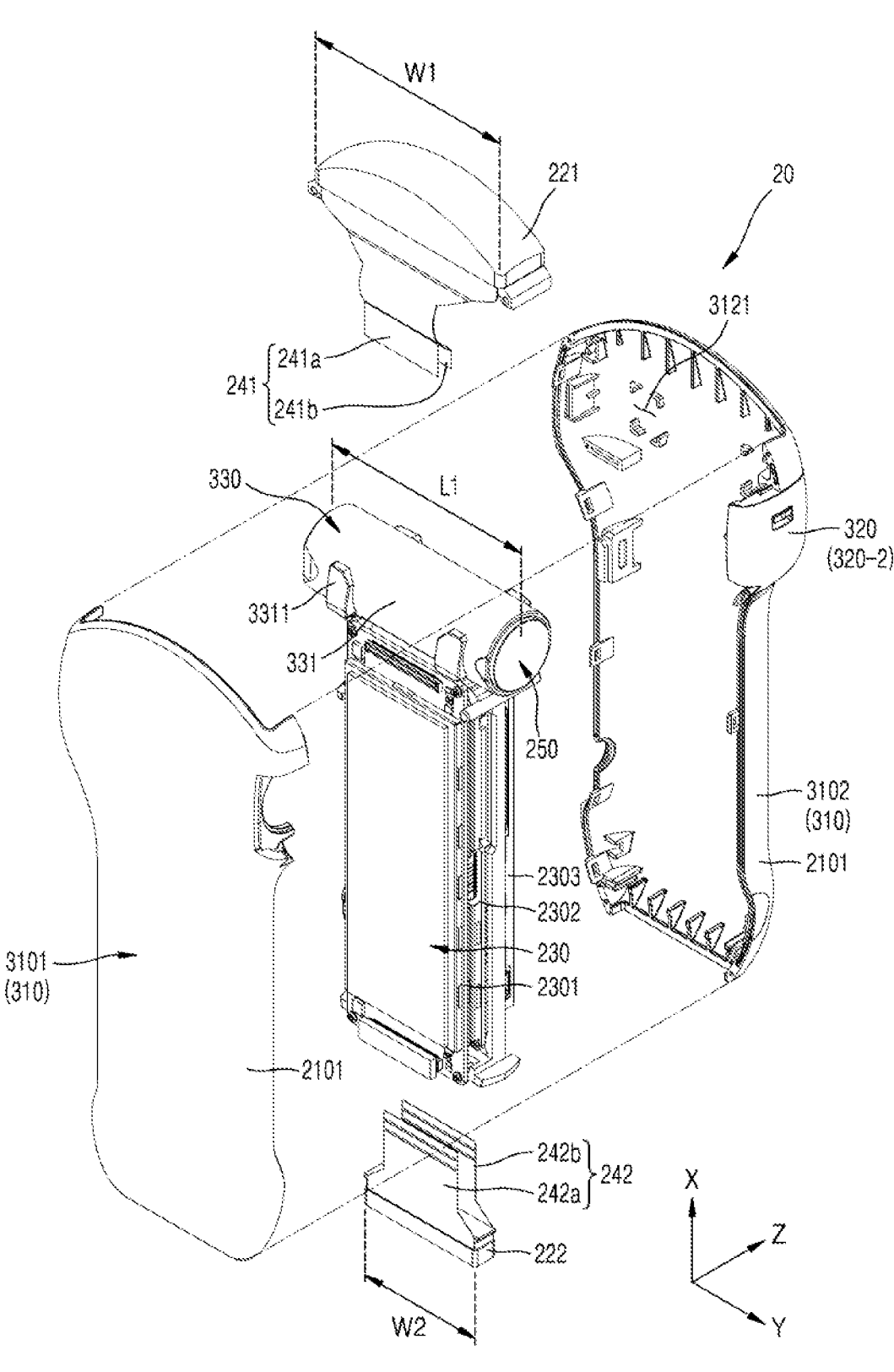
FIG. 3 is an exploded perspective view illustrating a wireless probe, according to an embodiment.

FIG. 2 is a perspective view illustrating the wireless probe 20, according to an embodiment. FIG. 3 is an exploded perspective view illustrating the wireless probe 20, according to an embodiment.

Referring to FIGS. 2 and 3, the wireless probe 20 according to an embodiment may include a housing 210, a first transducer 221, a circuit board 230, and a battery 250.

The housing 210 may have a length in a first direction X. The housing 210 may have a width in a second direction Y perpendicular to the first direction X, and may have a thickness in a third direction Z perpendicular to both the first direction X and the second direction Y. In the housing 210, a length in the first direction X may be greater than a width in the second direction Y, and the width in the second direction Y may be greater than a thickness in the third direction Z.

A width of the housing 210 in the second direction Y may vary according to a position in the first direction X. For example, a width of one end of the housing 210 in the first direction X may be greater than a width of the other end of the housing 210 in the first direction X.

The first transducer 221 may be located at one end of the housing 210 in the first direction X. The first transducer 221 for transmitting and receiving an ultrasound wave toward a subject may include a plurality of transducer members.

The plurality of transducer members of the first transducer 221 may be arranged in the second direction Y. For example, the plurality of transducer members of the first transducer 221 may be convexly arranged along the second direction Y.

A second transducer 222 may be located at the other end of the housing 210 in the first direction X. The first transducer 221 may be located at one end of the housing 210 in the first direction X, and the second transducer 222 may be located at the other end of the housing 210 in the first direction X.

A plurality of transducer members of the second transducer 222 may be arranged in the second direction Y. For example, the plurality of transducer members of the second transducer 222 may be linearly arranged along the second direction Y.

A width W1 of the first transducer 221 in the second direction Y may be different from a width W2 of the second transducer 222 in the second direction Y. For example, the width W1 of the first transducer 221 in the second direction Y may be greater than the width W2 of the second transducer 222 in the second direction Y. In other words, the width W2 of the second transducer 222 in the second direction Y may be less than the width W1 of the first transducer 221 in the second direction Y.

The circuit board 230 may be located inside the housing 210. The circuit board 230 may be located inside a handle portion 2101 that is a portion of the housing 210 having a small width in the second direction Y. A width of the circuit board 230 in the second direction Y may be less than a width of the handle portion 2101 of the housing 210 in the second direction Y, and may be 80% or more of the width of the handle portion 2101 of the housing 210 in the second direction Y.

The circuit board 230 may be supported by a board support (not shown) located inside the housing 210. The board support may be an element separate from the housing 210, but the disclosure is not limited thereto, and the board support may be integrally formed with the housing 210.

The circuit board 230 may include a transmission/reception circuit for transmitting/receiving data to/from the first transducer 221 and the second transducer 222. The circuit board 230 may include a plurality of sub-circuit boards stacked along the third direction Z. For example, the circuit board 230 may include a first sub-circuit board 2301, a second sub-circuit board 2302, and a third sub-circuit board 2303. The first sub-circuit board 2301 may include a transmission/reception circuit, the second sub-circuit board 2302 may include a power circuit, and the third sub-circuit board 2303 may include a control circuit. However, a type of a circuit located on each sub-circuit board is not limited thereto, and may be appropriately changed as necessary.

The circuit board 230 may be located inside the housing 210, and may be electrically connected to at least one transducer. For example, the circuit board 230 may be electrically connected to the first transducer 221, and may be electrically connected to the second transducer 222. For example, the first sub-circuit board 2301 may be electrically connected to the first transducer 221, and may be electrically connected to the second transducer 222.

The circuit board 230 and at least one transducer may be electrically connected by at least one flexible circuit unit.

For example, the first transducer 221 may be electrically connected to the circuit board 230 by at least one first flexible circuit unit 241. For example, the plurality of transducer members of the first transducer 221 may be electrically connected to the circuit board 230 by at least one first flexible circuit unit 241. For example, the plurality of transducer members of the first transducer 221 may be electrically connected to the circuit board 230 by a plurality of first flexible circuit units 241a and 241b. However, the number of first flexible circuit units 241 is not limited thereto, and may be changed in consideration of the number of transducer members, etc.

For example, the second transducer 222 may be electrically connected to the circuit board 230 by at least one second flexible circuit unit 242. For example, the plurality of transducer members of the second transducer 222 may be electrically connected to the circuit board 230 by at least one second flexible circuit unit 242. For example, the plurality of transducer members of the second transducer 222 may be electrically connected to the circuit board 230 by a plurality of second flexible circuit units 242a and 242b. However, the number of second flexible circuit units 242 is not limited thereto, and may be changed in consideration of the number of transducer members, etc.

The battery 250 may be located inside the housing 210, and may provide power for operating the wireless probe 20. The battery 250 may provide power to the first and second transducers 221 and 222 of the wireless probe 20. The battery 250 may be a rechargeable secondary battery. In another example, the battery 250 may be a non-rechargeable battery.

The battery 250 may have a shape that is long in a longitudinal direction. For example, a length of the battery 250 may be greater than a diameter (or a width) of the battery 250. For example, a length of the battery 250 may be greater than twice a diameter of the battery 250. A length of the battery 250 may be greater than three times a diameter of the battery 250.

Figure 10:
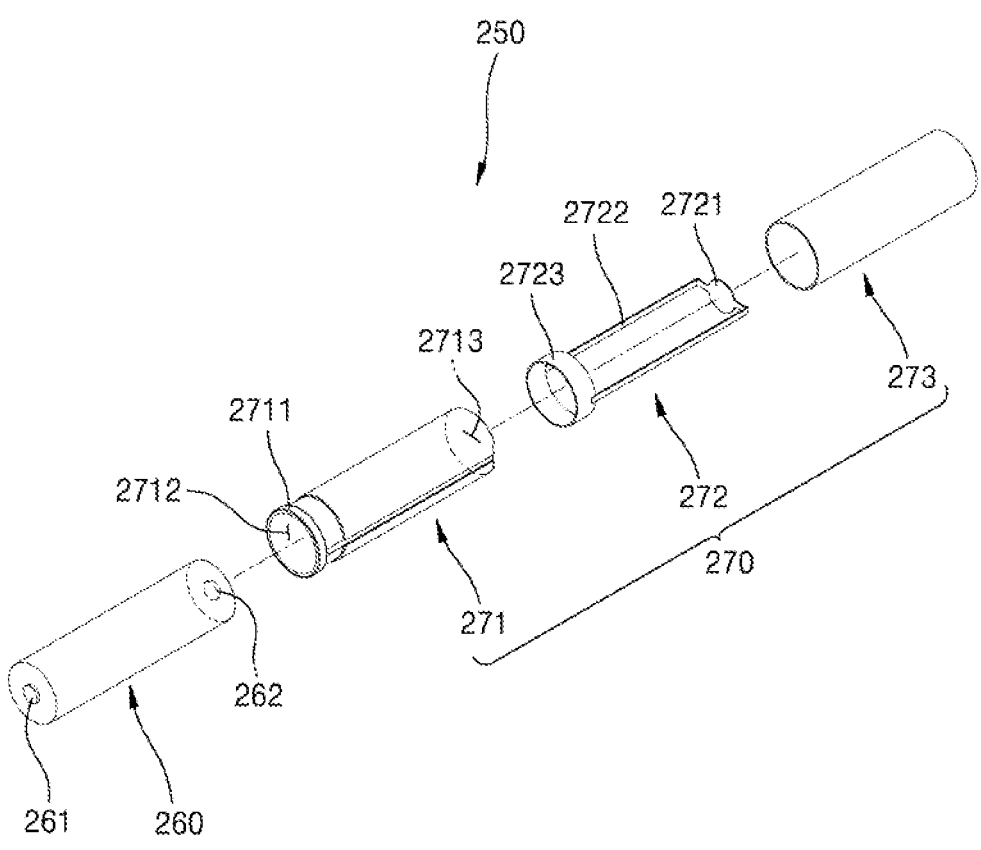
FIG. 10 is an exploded perspective view illustrating the battery of FIG. 9.

The battery 250 may include a standardized battery body 260 (see FIG. 10). For example, the battery body 260 may have a cylindrical shape. For example, the battery body 260 may be a cylindrical battery having a diameter of 18 mm and a length of 65 mm. Because the standardized battery 250 is used as the battery body 260, a user may easily obtain the battery body 260 for supplying power to the wireless probe 20.

A length L1 of the battery 250 in the second direction Y may correspond to the width W1 of the first transducer 221 in the second direction Y. For example, a difference between the width W1 of the first transducer 221 along the second direction Y and the length L1 of the battery 250 along the second direction Y may be 20% or less of the length L1 of the battery 250 along the second direction Y. The length L1 of the battery in the second direction Y may be greater than the width W2 of the second transducer 222 in the second direction Y. The length L1 of the battery 250 according to the second direction Y may be greater than 1.2 times the width W2 of the second transducer 222 in the second direction Y.

The wireless probe 20 may perform an ultrasound scan operation by receiving power from the battery 250 located therein, without receiving power from the outside. However, because the wireless probe 20 receives power from the battery 250, the battery 250 needs to be charged or replaced with a charged battery 250 before being completely discharged.

The wireless probe 20 according to an embodiment may provide a structure in which the user may easily replace the battery 250 and waterproof performance may be maintained.

Figure 4:
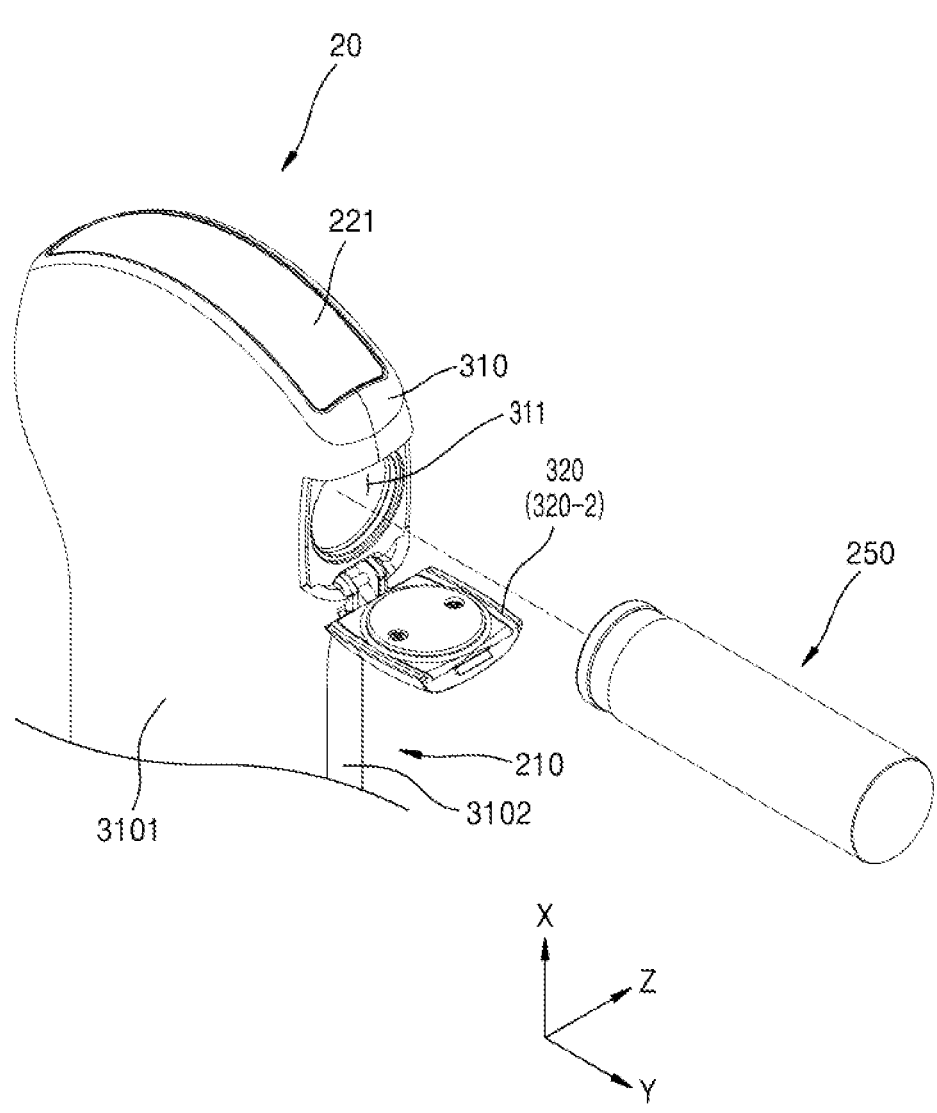
FIG. 4 is a perspective view illustrating a state where a battery is separated from a wireless probe, according to an embodiment.
Figure 5:
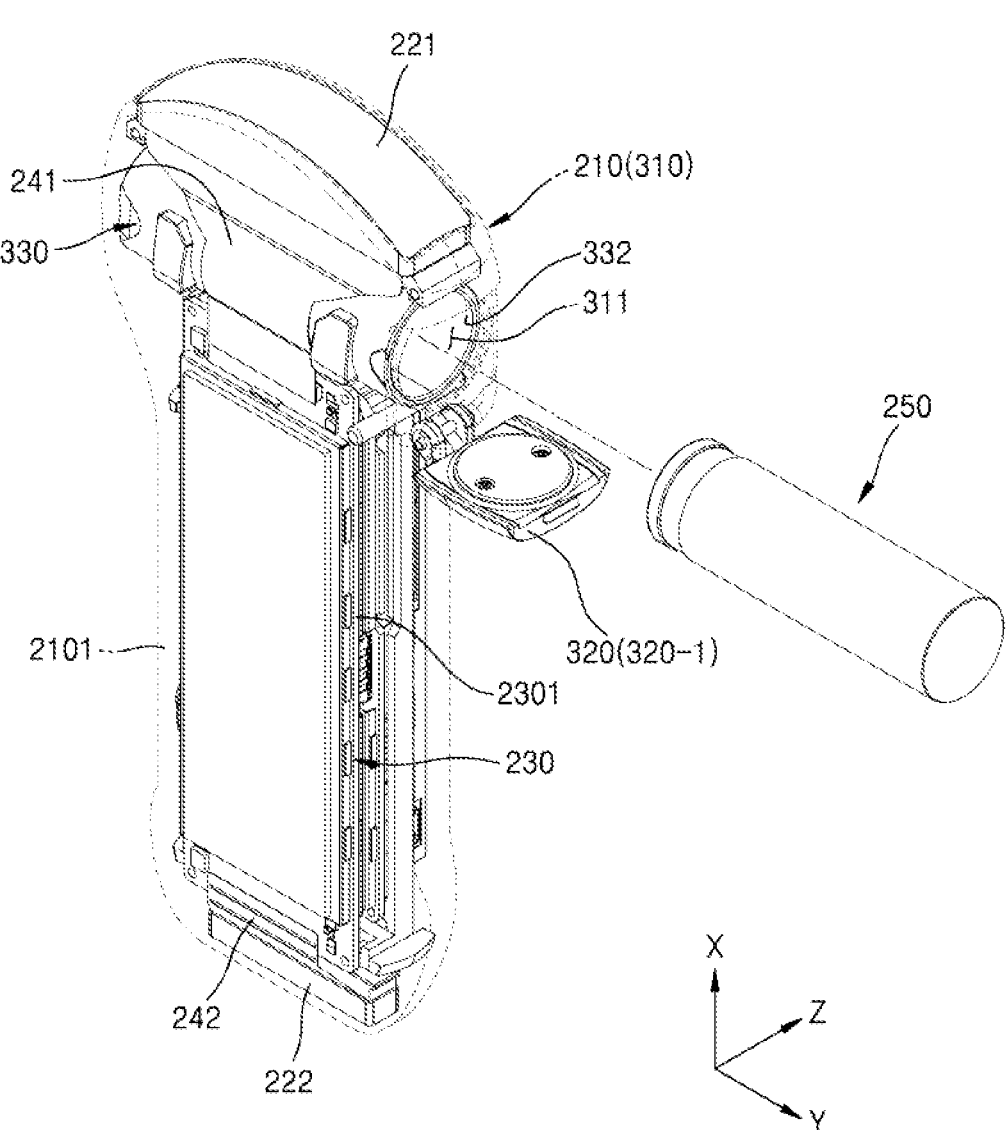
FIG. 5 is a perspective view illustrating an internal configuration of a housing in the wireless probe of FIG. 4.

FIG. 4 is a perspective view illustrating a state where the battery 250 is separated from the wireless probe 20, according to an embodiment. FIG. 5 is a perspective view illustrating an internal configuration of the housing 210 in the wireless probe 20 of FIG. 4.

Referring to FIGS. 4 and 5, the housing 210 of the wireless probe 20 according to an embodiment may be configured to allow the battery 250 to be inserted and separated along the second direction Y. In other words, the battery 250 may be configured to be inserted into and separated from the housing 210 along the second direction Y parallel to a longitudinal direction of the battery 250.

The housing 210 according to an embodiment may include an outer housing 310, a housing cap 320, and a battery accommodating unit 330.

The outer housing 310 forms the exterior of the wireless probe 20, and includes an opening 311 provided at one end in the second direction Y. The opening 311 may have a shape corresponding to a cross-sectional shape of the battery 250. For example, a diameter of the opening 311 may correspond to a diameter of the battery 250.

The outer housing 310 may include a plurality of housing members 3101 and 3102. For example, the outer housing 310 may include a plurality of housing members 3101 and 3102 that may be assembled in the third direction Z perpendicular to both the first direction X and the second direction Y.

The housing cap 320 may form the exterior of the wireless probe 20 along with the outer housing 310, and may be configured to open and close the opening 311. A configuration of the housing cap 320 will be described below with reference to FIG. 12A.

The battery accommodating unit 330 may be located inside the outer housing 310. For example, the battery accommodating unit 330 may be located inside the outer housing 310 to be connected to the opening 311 of the outer housing 310. The battery accommodating unit 330 may include a position setting portion 3311 inserted into a position setting portion 3121 of the outer housing 310. Due to the position setting portion 3121 of the outer housing 310 and the position setting portion 3311 of the battery accommodating unit 330, the battery accommodating unit 330 may be maintained at a constant position inside the outer housing 310.

The battery accommodating unit 330 includes one end 332 into which the battery 250 may be inserted. The one end 332 of the battery accommodating unit 330 may face the opening 311 of the outer housing 310.

The battery accommodating unit 330 may have an inner space in which at least a part of the battery 250 inserted through the opening 311 is accommodated.

The battery accommodating unit 330 may be configured so that the battery 250 is inserted and separated along the second direction Y. For example, the battery accommodating unit 330 may extend along the second direction Y. For example, the battery accommodating unit 330 may have a cross-sectional shape corresponding to a cross-sectional shape of the battery 250. For example, when the battery 250 has a circular cross-sectional shape, the battery accommodating unit 330 may have a circular cross-sectional shape.

When the battery 250 is inserted into the outer housing 310 or separated from the outer housing 310, the battery accommodating unit 330 may guide the battery 250 to move along a certain direction. For example, the battery accommodating unit 330 may guide the battery 250 to move in the second direction Y. To this end, in an example, the battery accommodating unit 330 may extend along the second direction Y.

The battery accommodating unit 330 may be configured to define a position of the battery 250 in the outer housing 310. For example, the battery accommodating unit 330 may be located between the first transducer 221 and the circuit board 230.

Although the battery accommodating unit 330 is an element separate from the outer housing 310 in FIGS. 4 and 5, the disclosure is not limited thereto. For example, the battery accommodating unit 330 and the outer housing 310 may be one element. Also, although the battery 250 may be inserted into and separated from the right side of the wireless probe 20 in FIGS. 4 and 5, the disclosure is not limited thereto, and various modifications may be made. For example, the battery 250 may be inserted into and separated from the left side of the wireless probe 20.

Figure 6:
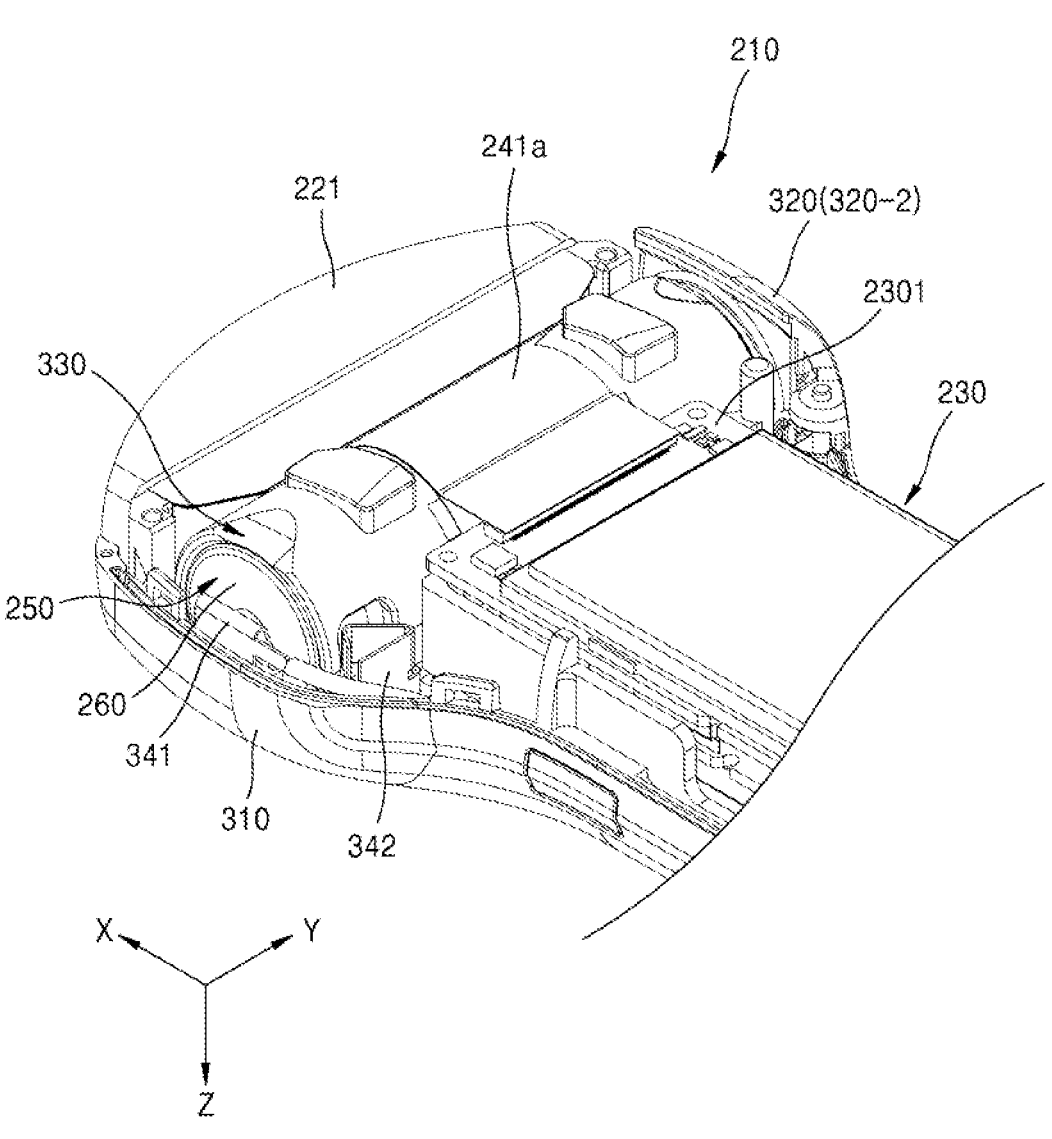
FIG. 6 is a perspective view illustrating a battery accommodating unit in a wireless probe, according to an embodiment.
Figure 7:
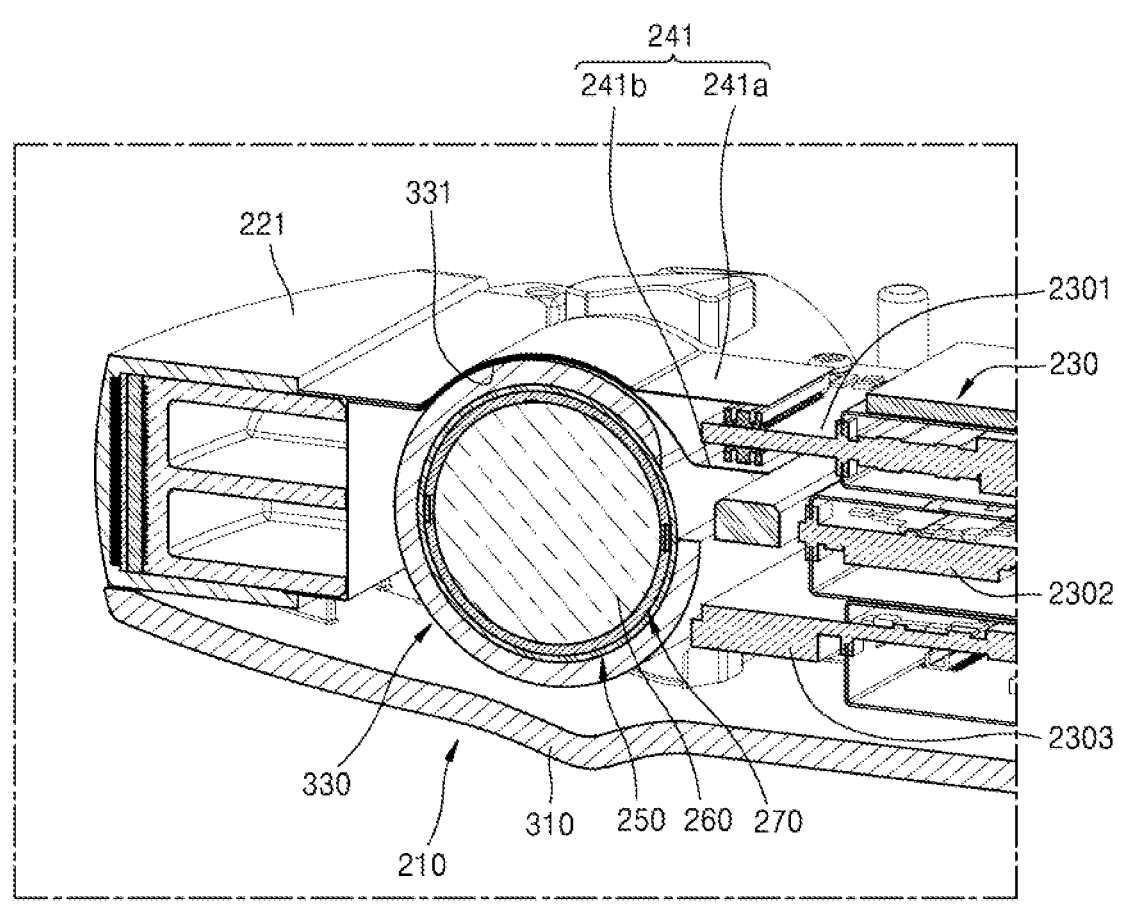
FIG. 7 is a cross-sectional perspective view illustrating the wireless probe of FIG. 6.
Figure 8:
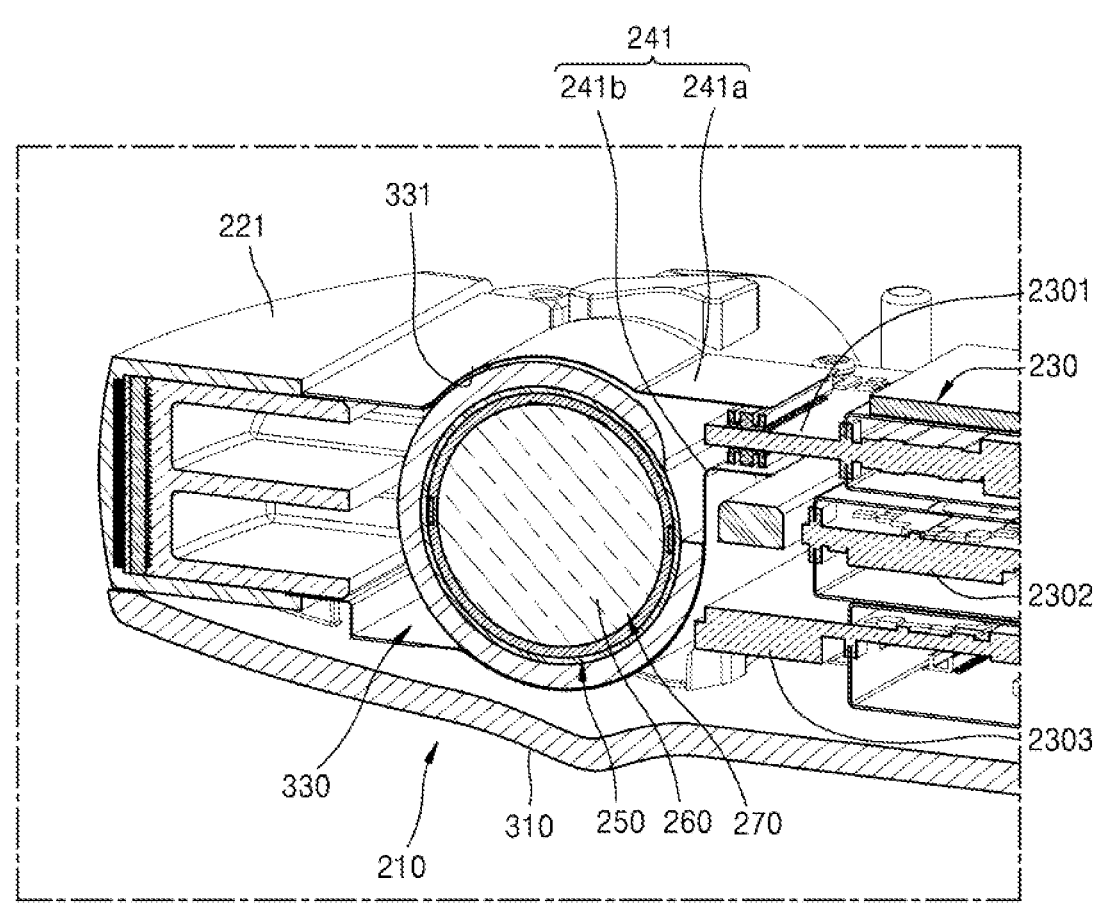
FIG. 8 is a perspective view illustrating a wireless probe, according to an embodiment.

FIG. 6 is a perspective view illustrating the battery accommodating unit 330 in the wireless probe 20, according to an embodiment. FIG. 7 is a cross-sectional perspective view illustrating the wireless probe 20 of FIG. 6. FIG. 8 is a perspective view illustrating the wireless probe 20, according to an embodiment. In FIGS. 6 to 8, for convenience of illustration, a part of the housing member 3101 of the outer housing 310 is not shown.

Referring to FIGS. 6 and 7, in the wireless probe 20 according to an embodiment, the battery 250 may be inserted into the battery accommodating unit 330. For example, a side surface of the battery 250 may be surrounded by the battery accommodating unit 330. The first flexible circuit unit 241 may be located to bypass the battery accommodating unit 330. While the battery 250 is inserted into or separated from the battery accommodating unit 330, the battery accommodating unit 330 may prevent contact between the first flexible circuit unit 241 and the battery 250. Accordingly, damage to the first flexible circuit unit 241 may be prevented.

The first flexible circuit unit 241 may be located to pass through a side portion 331 of the battery accommodating unit 330. For example, the first flexible circuit unit 241 may surround a part of the side portion 331 of the battery accommodating unit 330. One end of the first flexible circuit unit 241 may be connected to the first transducer 221, and the other end of the first flexible circuit unit 241 may be connected to the circuit board 230.

A plurality of first flexible circuit units 241 may be provided. For example, one first flexible circuit unit 241b from among the plurality of first flexible circuit units 241a and 241b may surround the side portion 331 of the battery accommodating unit 330. The other first flexible circuit unit 241a from among the plurality of first flexible circuit units 241a and 241b may be in close contact with the one first flexible circuit unit 241b. The other first flexible circuit unit 241a from among the plurality of first flexible circuit units 241a and 241b may surround a part of the first flexible circuit unit 241b.

The plurality of first flexible circuit units 241a and 241b may be electrically connected to different positions on the circuit board 230. For example, the first flexible circuit unit 241*b* may be connected to one surface, for example, a bottom surface, of the first sub-circuit board 2301, and the other first flexible circuit unit 241*a* may be connected to the other surface, for example, a top surface, of the first sub-circuit board 2301.

However, a position of the first flexible circuit unit 241 in the wireless probe 20 is not limited thereto, and may vary. For example, as shown in FIG. 8, each of the plurality of first flexible circuit units 241*a* and 241*b* may surround a part of the side portion 331 of the battery accommodating unit 330. The first flexible circuit unit 241*b* and the other first flexible circuit unit 241*a* from among the plurality of first flexible circuit units 241*a* and 241*b* may be spaced apart from each other and may be connected to the circuit board 230.

Figure 9:
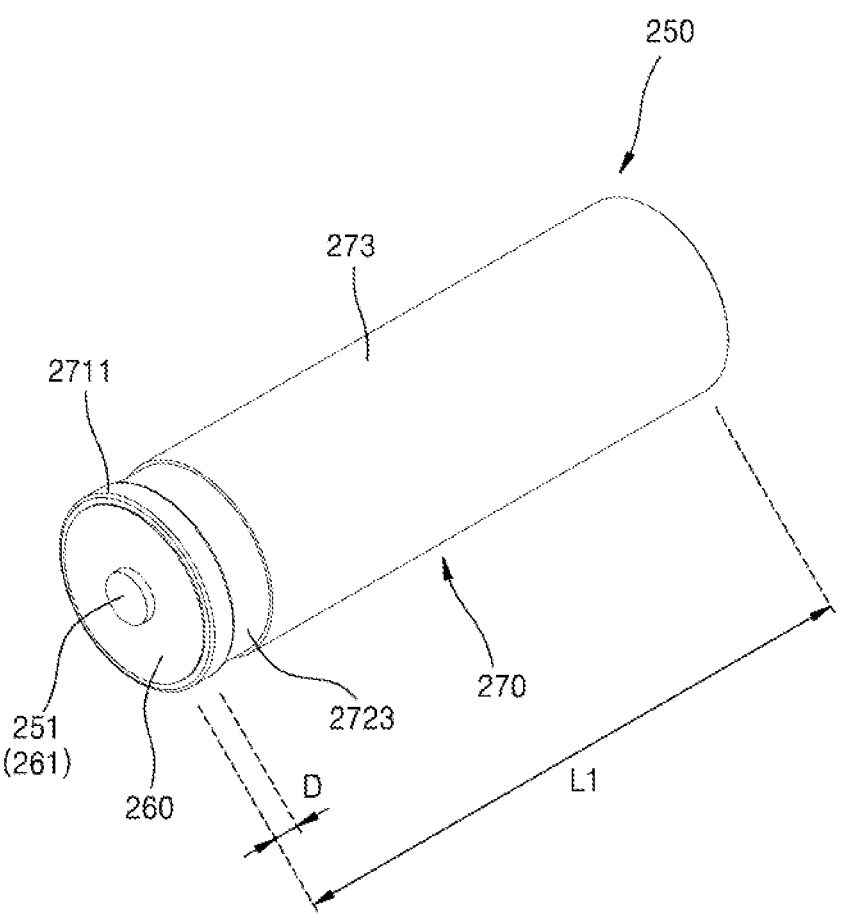
FIG. 9 is a perspective view illustrating a battery used in a wireless probe, according to an embodiment.
Figure 11:
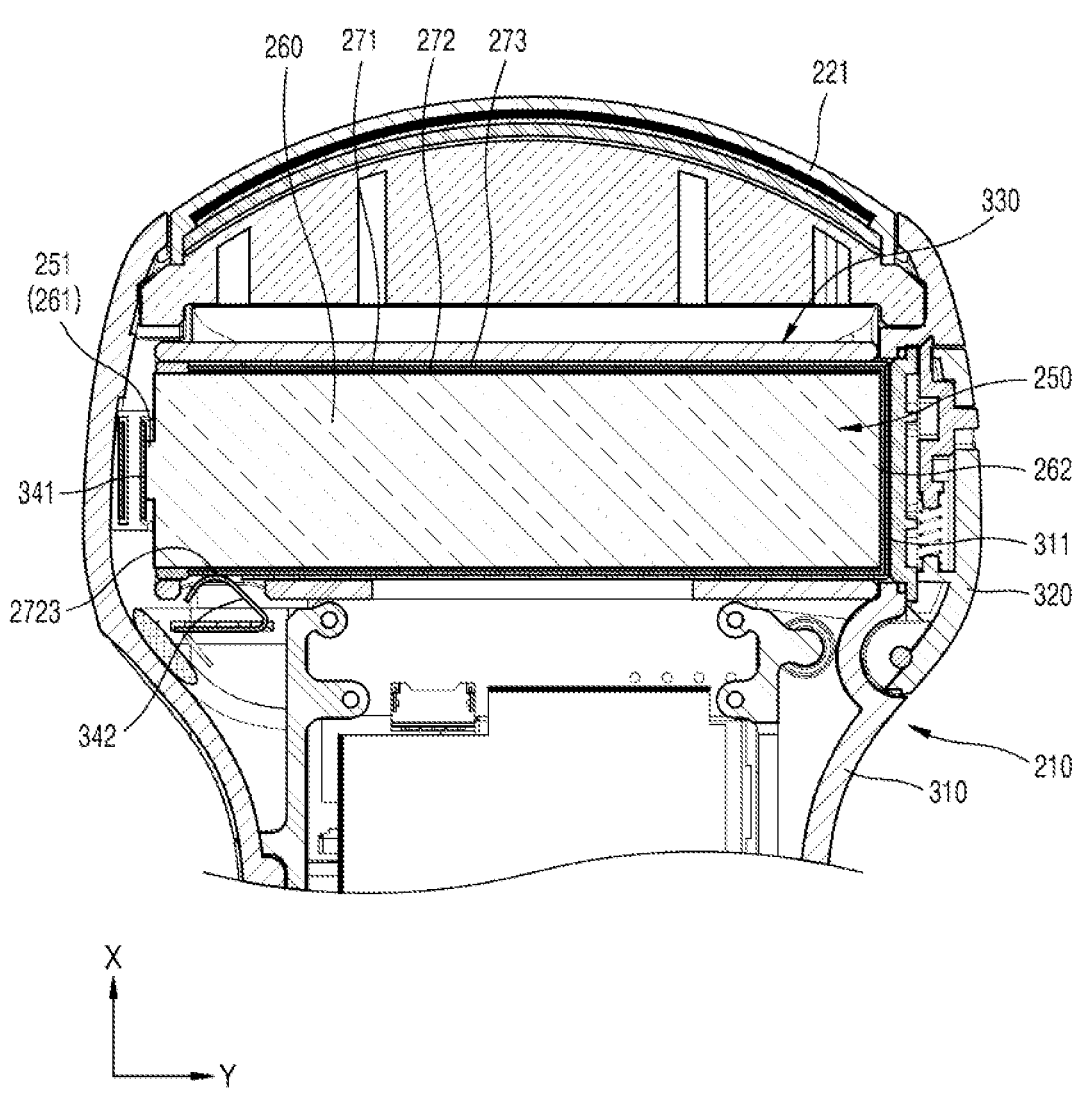
FIG. 11 is a cross-sectional view illustrating a part of the wireless probe of FIG. 6 taken along a plane perpendicular to a third direction.

FIG. 9 is a perspective view illustrating the battery 250 used in the wireless probe 20, according to an embodiment. FIG. 10 is an exploded perspective view illustrating the battery 250 of FIG. 9. FIG. 11 is a cross-sectional view illustrating a part of the wireless probe 20 of FIG. 6 taken along a plane perpendicular to the third direction Z.

Referring to FIGS. 9 to 11, the battery 250 according to an embodiment may be located so that a first electrode portion 251 and a second electrode portion 2723 are adjacent to each other. The first electrode portion 251 and the second electrode portion 2723 may have different polarities. In the battery 250, the first electrode portion 251 and the second electrode portion 2723 may be located adjacent to each other at the front in an insertion direction of the battery 250.

A distance D between the first electrode portion 251 and the second electrode portion 2723 may be less than ½ of the length L1 of the battery 250. The distance D between the first electrode portion 251 and the second electrode portion 2723 may be less than ⅕ of the length L1 of the battery 250. The distance D between the first electrode portion 251 and the second electrode portion 2723 may be less than ⅒ of the length L1 of the battery 250. The distance D between the first electrode portion 251 and the second electrode portion 2723 may be 10 mm or less. The distance D between the first electrode portion 251 and the second electrode portion 2723 may be 5 mm or less. The length L1 of the battery 250 may be the length L1 of the battery 250 along the second direction Y.

The battery 250 may include the battery body 260 and an electrode adjusting assembly 270 for complementing an electrode position of the battery body 260.

In the battery body 260, a first electrode 261 and a second electrode 262 having different polarities may be provided at both ends in the longitudinal direction. The first electrode 261 may be located at one end of the battery body 260, and the second electrode 262 may be located at the other end of the battery body 260. In an example, the first electrode 261 may be a positive electrode, and the second electrode 262 may be a negative electrode. In another example, the first electrode 261 may be a negative electrode, and the second electrode 262 may be a positive electrode.

The battery body 260 may be a standard battery. For example, the battery body 260 may have a shape that is long in the longitudinal direction. For example, a length of the battery body 260 may be greater than a diameter (or a width) of the battery body 260. For example, a length of the battery body 260 may be greater than twice a diameter of the battery body 260. A length of the battery body 260 may be greater than three times a diameter of the battery body 260. The battery body 260 may have a cylindrical shape. For example, the battery body 260 may be the cylindrical battery 250 having a diameter of 18 mm and a length of 65 mm.

The electrode adjusting assembly 270 may expose the first electrode 261 of the battery body 260 to the outside to form the first electrode portion 251. In other words, the first electrode 261 exposed to the outside of the electrode adjusting assembly 270 may function as the first electrode portion 251 of the battery 250.

The electrode adjusting assembly 270 may cover the second electrode 262 of the battery body 260. The electrode adjusting assembly 270 may be electrically connected to the second electrode 262 to form the second electrode portion 2723 adjacent to the first electrode portion 251. Because the electrode adjusting assembly 270 may allow electrical contact through the second electrode portion 2723 adjacent to the first electrode portion 251 while covering the second electrode portion 2723 to prevent external exposure of the second electrode portion 2723, the waterproof performance of the wireless probe 20 may be improved.

To this end, in an example, the electrode adjusting assembly 270 may include an inner insulator 271, an electrode moving body 272, and an outer insulator 273.

The inner insulator 271 may surround a side surface of the battery body 260 and expose the first electrode 261 and the second electrode 262 of the battery body 260 through both ends of the inner insulator 271.

The inner insulator 271 may have an internal shape corresponding to a side shape of the battery body 260. The inner insulator 271 may include an insulating ring 2711 for insulation between the first electrode portion 251 and the second electrode portion 2723. The insulating ring 2711 of the inner insulator 271 may have a larger outer diameter than other portions of the inner insulator 271.

The inner insulator 271 may include first and second openings 2712 and 2713 through which the first electrode 261 and the second electrode 262 of the battery body 260 are exposed. The first electrode 261 of the battery body 260 may be exposed through the first opening 2712 of the inner insulator 271, and the second electrode 262 of the battery body 260 may be exposed through the second opening 2713 of the inner insulator 271.

The electrode moving body 272 may include an electrode contact portion 2721 contacting the second electrode 262 exposed through the inner insulator 271, the second electrode portion 2723 located at a position spaced apart from the electrode contact portion 2721, and an extending portion 2722 electrically connecting the electrode contact portion 2721 to the second electrode portion 2723. The electrode moving body 272 may include a conductive material for electrical connection with the second electrode 262.

The second electrode portion 2723 may have a ring shape surrounding the inner insulator 271. The extending portion 2722 may extend in the longitudinal direction of the battery 250. However, a shape of the second electrode portion 2723 and an extending direction of the extending portion 2722 are not limited thereto, and may vary.

The outer insulator 273 may surround a side surface of the inner insulator 271. The extending portion 2722 of the electrode moving body 272 may be located between the outer insulator 273 and the inner insulator 271. The outer insulator 273 may cover the electrode contact portion 2721 of the electrode moving body 272. The outer insulator 273 may expose the second electrode portion 2723 of the electrode moving body 272.

The outer insulator 273 may exposed one end of the battery body 260 where the first electrode 261 is formed to the outside, and may cover a side surface of the battery body 260 and the other end of the battery body 260 where the second electrode 262 is formed.

The battery 250 may be configured so that the second electrode portion 2723 forms a concave portion. For example, an outer diameter of the second electrode portion 2723 may be less than an outer diameter of the outer insulator 273. For example, an outer diameter of the second electrode portion 2723 may be less than an outer diameter of the insulating ring 2711 of the inner insulator 271. In other words, the second electrode portion 2723 having a smaller outer diameter than the outer insulator 273 and the inner insulator 271 may form a concave portion of the battery 250.

Referring to FIGS. 6 and 11, in the wireless probe 20 according to an embodiment, the battery 250 may be configured so that an end where the first electrode portion 251 is formed is first inserted into the opening 311 of the outer housing 310. For example, in the battery accommodating unit 330, a first electrode terminal 341 and a second electrode terminal 342 for electrical connection with the battery 250 may be installed.

The first electrode terminal 341 may electrically contact the first electrode portion 251 of the battery 250. The second electrode terminal 342 may electrically contact the second electrode portion 2723 of the battery 250.

Directions of the first electrode terminal 341 and the second electrode terminal 342 may be perpendicular to each other. For example, the first electrode terminal 341 may be located along a direction parallel to the insertion direction of the battery 250. The second electrode terminal 342 may be located along a direction perpendicular to the insertion direction of the battery 250.

The second electrode terminal 342 may be inserted into the concave portion of the battery 250 where the second electrode portion 2723 is located. Because the second electrode terminal 342 is inserted into the concave portion of the battery 250, an insertion position of the battery 250 electrically connected to the wireless probe 20 may be maintained, and while a user mounts the battery 250, the user may easily recognize whether the battery 250 has reached the insertion position.

As described above, in the wireless probe 20, the first and second electrode portions 251 and 2723 of the battery 21560 may be located far from the opening 311 of the outer housing 310. For example, a distance between the first and second electrode portions 251 and 2723 of the battery 250 and the opening 311 of the outer housing 310 may increase. For example, when the battery 250 is inserted into the battery accommodating unit 330, a distance between the second electrode portion 2723 of the battery and the opening 311 of the outer housing 310 along the second direction Y may be greater than a distance between the second electrode 262 of the battery body 260 and the opening 311 of the outer housing 310 along the second direction Y.

Accordingly, the waterproof performance of the wireless probe 20 may be improved. For example, even when water penetrates into the opening 311 of the outer housing 310, a distance through which the penetrated water reaches the first and second electrode portions 251 and 2723 of the battery 250 is increased, thereby improving waterproof performance.

However, a structure of the battery 250 is not limited thereto, and may include the battery body 260 without the electrode adjusting assembly 270. In this case, a position of the second electrode terminal 342 may be changed.

Figure 12A:
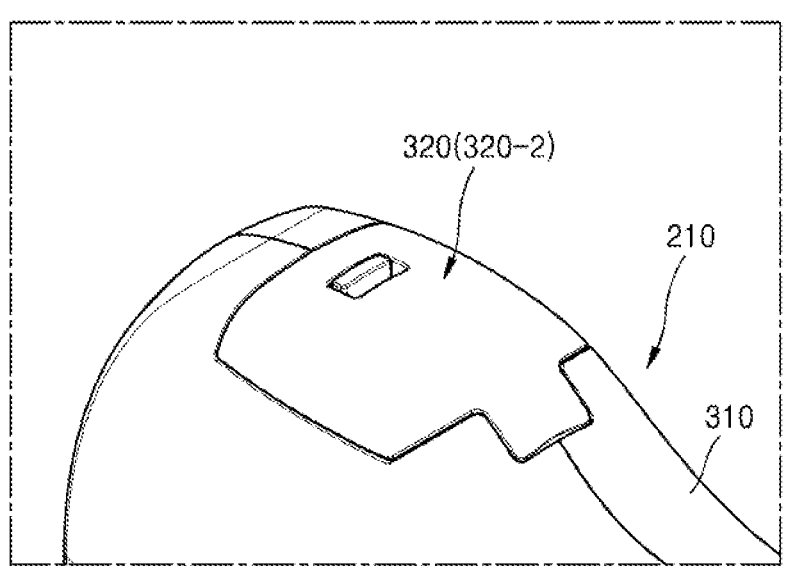
FIGS. 12A and 12B are perspective views illustrating a housing cap in a wireless probe, according to an embodiment.
Figure 12B:
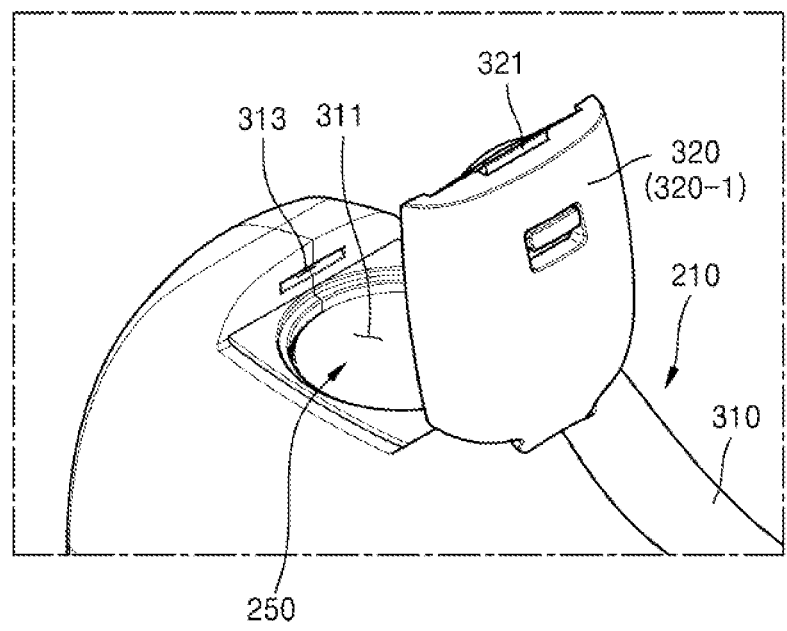
Figure 13A:
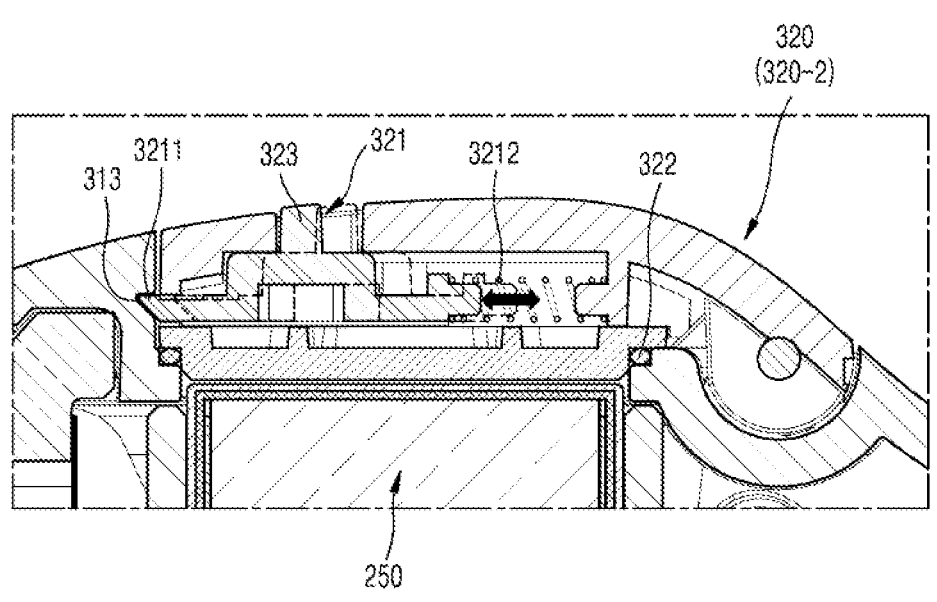
FIGS. 13A and 13B are cross-sectional views illustrating the wireless probe of FIGS. 12A and 12B.
Figure 13B:
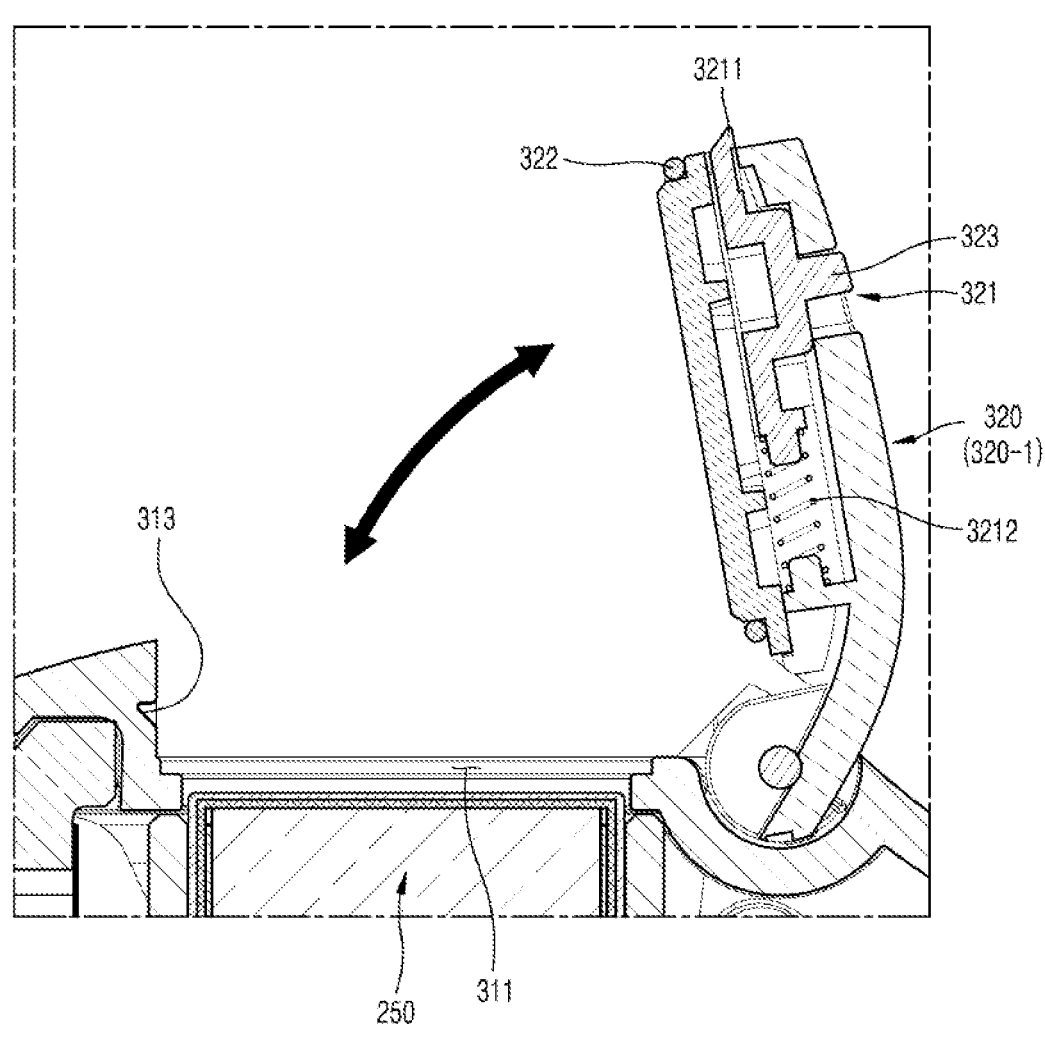
Figure 14:
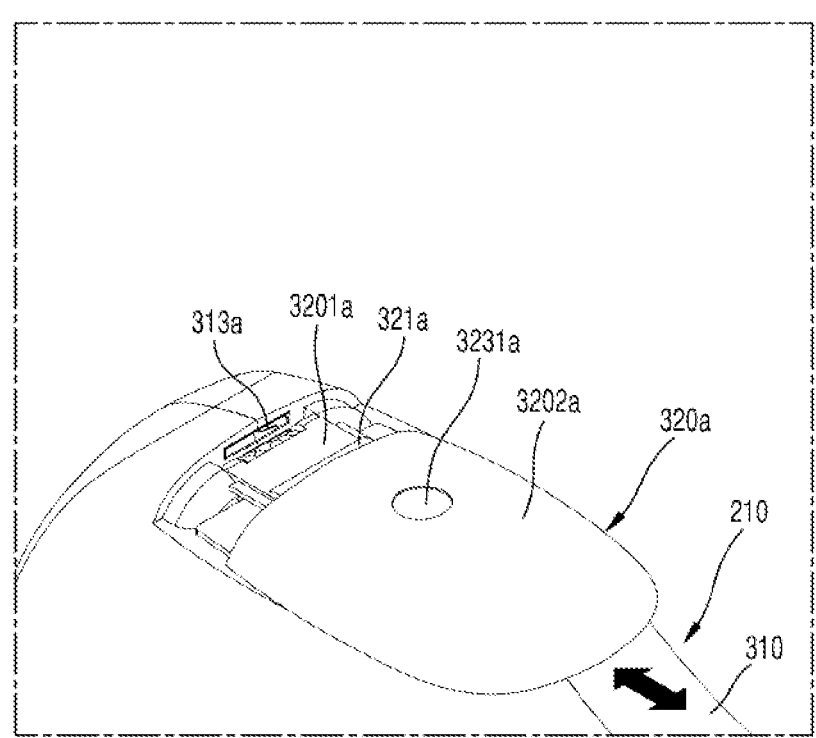
FIG. 14 is a view illustrating another example of a housing cap in a wireless probe, according to an embodiment.
Figure 15:
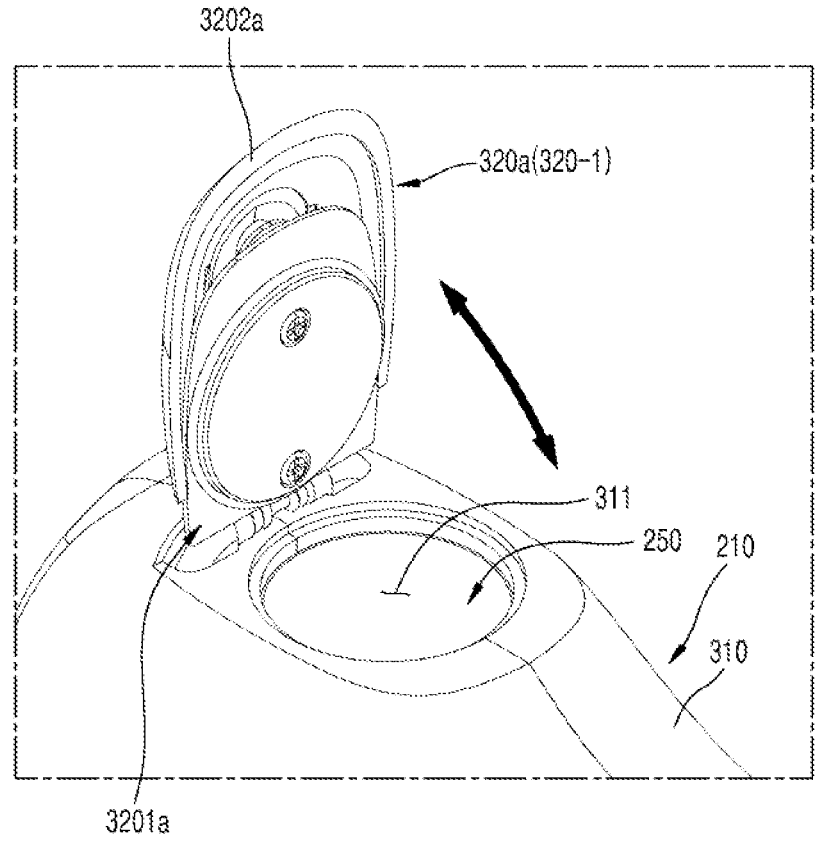
FIG. 15 is a view for describing an operation of the housing cap of FIG. 14.
Figure 16:
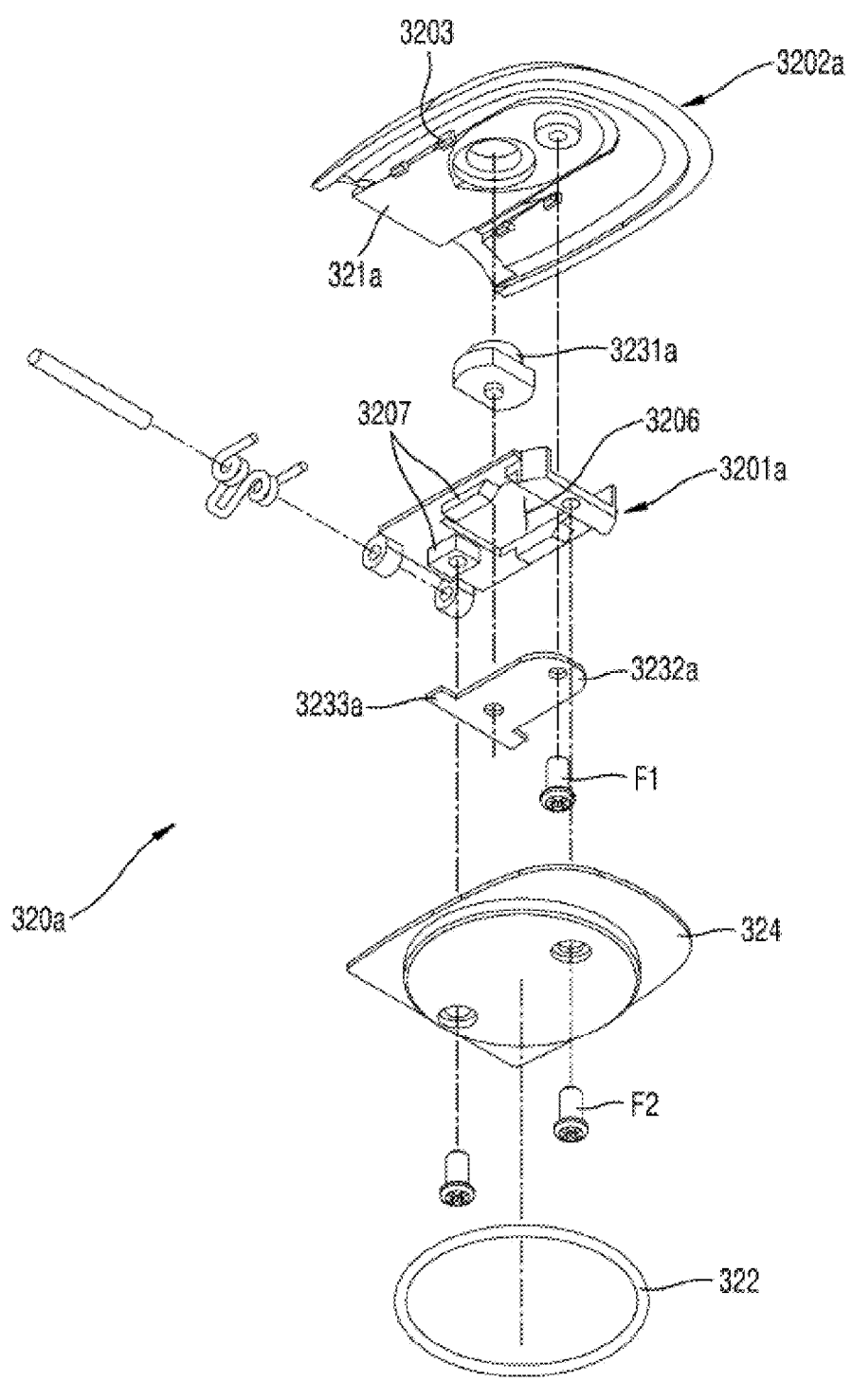
FIG. 16 is an exploded perspective view illustrating the housing cap of FIG. 14.

FIGS. 12A and 12B are perspective views illustrating the housing cap 320 in the wireless probe 20, according to an embodiment. FIGS. 13A and 13B are cross-sectional views illustrating the wireless probe 20 of FIGS. 12A and 12B.

Referring to FIGS. 12A and 12B, the housing 210 according to an embodiment includes the housing cap 320 having an open position 3201 for opening the opening 311 of the outer housing 310 and a closed position 320-2 for closing the opening 311. The housing cap 320 may be configured to selectively close the opening 311 of the outer housing 310. The housing cap 320 may be supported on the outer housing 310 to pivot between the open position 320-1 for opening the opening 311 and the closed position 320-2 for closing the opening 311.

Referring to FIGS. 13A and 13B, the housing cap 320 may include a locking member 321 configured to maintain the closed position 320-2. A locked state of the housing cap 320 may be maintained by the locking member 321. The locking member 321 may include a locking protrusion 3211 that may be inserted into a locking groove 313 of the housing 210, and a pressing member 3212 configured to press the locking protrusion 3211 so that the locking protrusion 3211 protrudes from a body of the housing cap 320.

A sealing member 322 for preventing penetration of water between the outer housing 310 and the housing cap 320 may be located on at least one of the outer housing 310 and the housing cap 320. For example, the housing cap 320 may further include the sealing member 322 located on a portion facing the opening 311 of the housing 210. The sealing member 322 may surround the opening 311 of the outer housing 310.

As shown in FIG. 13A, when the locking member 321 is inserted into the locking groove 313, the sealing member 322 may be compressed and deformed by the housing 210 and the body of the housing cap 320. Accordingly, water may be prevented from passing between the housing cap 320 and the housing 210 and penetrating into the battery 250 located inside the housing 210.

The locking member 321 may include a manipulation member 323 to facilitate the release of a locked state by the housing cap 320. For example, the manipulation member 323 may be a manipulation protrusion connected to the locking protrusion 3211 and exposed to the outside of the body of the housing cap 320. The user may easily move the locking protrusion 3211 in a direction opposite to a protruding direction by manipulating the manipulation member 323. For example, the user may move the manipulation member 323 backward with a force greater than a force pressed by the pressing member 3212, to separate the locking protrusion 3211 of the locking member 321 from the locking groove 313 of the housing 210.

Figure 17:
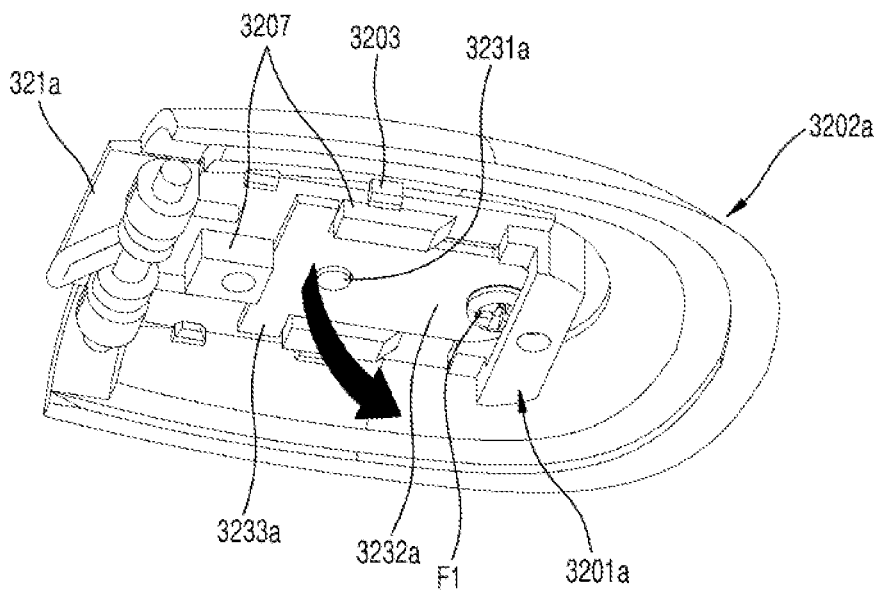
FIG. 17 is a view for describing a lower structure of the housing cap of FIG. 14.

However, a structure and a function of the housing cap 320 are not limited thereto, and may vary. FIGS. 14 to 24 are views illustrating other examples of a housing cap (e.g., 320a, 320b, 320c, and 320d) in the wireless probe 20, according to an embodiment. In FIG. 17, for convenience of explanation, a lower base 324 is not shown.

Referring to FIGS. 14 to 17, the wireless probe 20 according to another embodiment may include a housing cap 320a configured to close the opening 311 of the outer housing 310.

The housing cap 320a may include a body 3201a that is rotatable with respect to the outer housing 310 and a cover member 3202a that is slidable with respect to the body 3201a.

The cover member 3202a may include a guide portion 3203 provided on an inner surface to be slidable with respect to the body 3201a. A locking member 321a configured so that the housing cap 320a is maintained at the closed position 320-2 may be provided at an end of the cover member 3202a. The locking member 321a may be inserted into a locking groove 313a of an outer housing 310a.

A button 3231a that is vertically movable and an elastic plate 3232a that provides a force for restoring the button 3231a to its original position when the button 3231a is pressed may be located on the cover member 3202a. The elastic plate 3232a may be fixed by a fixing member F1, and one end of the elastic plate 3232a may be bent in a cantilever shape.

The body 3201a may include a through-hole 3206 through which the button 3231a and the elastic plate 3232a contact each other. The lower base 324 provided to be inserted into the opening 311 of the outer housing 310 may be fixed to a lower portion of the body 3201a. The body 3201a and the lower base 324 may be fixed by a fixing member F2. The sealing member 322 may be located on the lower base 324.

The housing cap 320a may be configured to selectively slide only when the button 3231a is pressed. For example, the elastic plate 3232a may include an interference protrusion 3233a protruding in a direction perpendicular to a sliding direction. A stopper 3207 for blocking sliding of the interference protrusion 3233a may be provided on the body 3201a.

As shown in FIG. 17, when the button 3231a is pressed downward and the elastic plate 3232a is bent downward, the interference protrusion 3233a may be separated from the stopper 3207 and thus, the cover member 3202a may be able to slide from the body 3201a.

Figure 18:
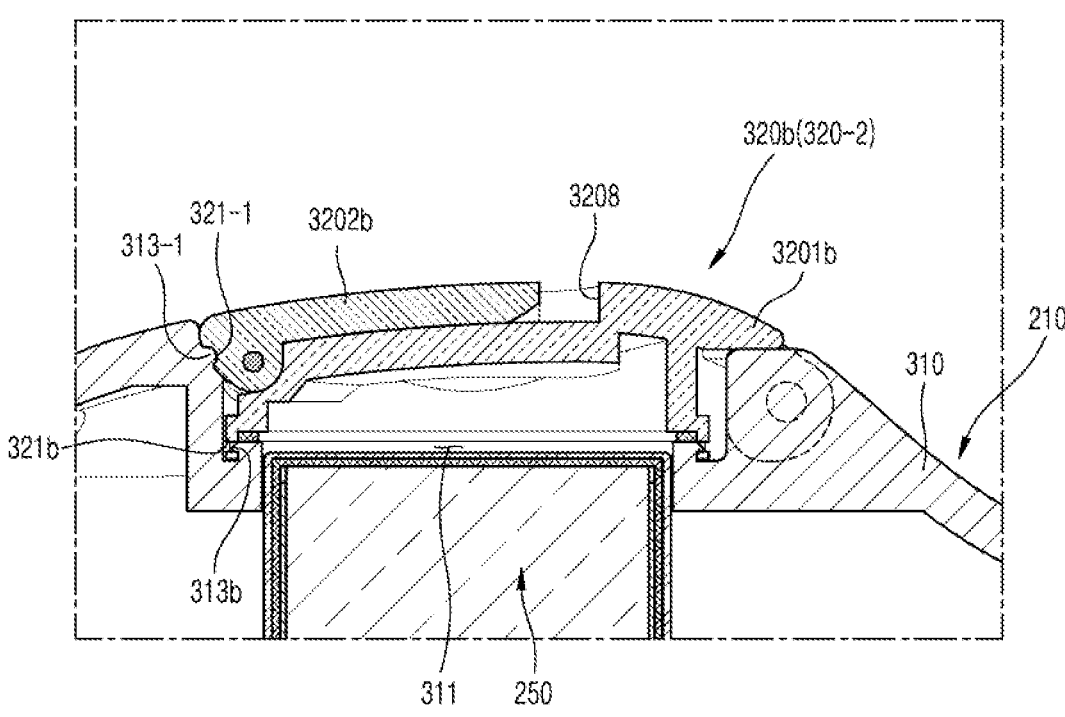
FIG. 18 is a cross-sectional view illustrating another example of a housing cap in a wireless probe, according to an embodiment.
Figure 19:
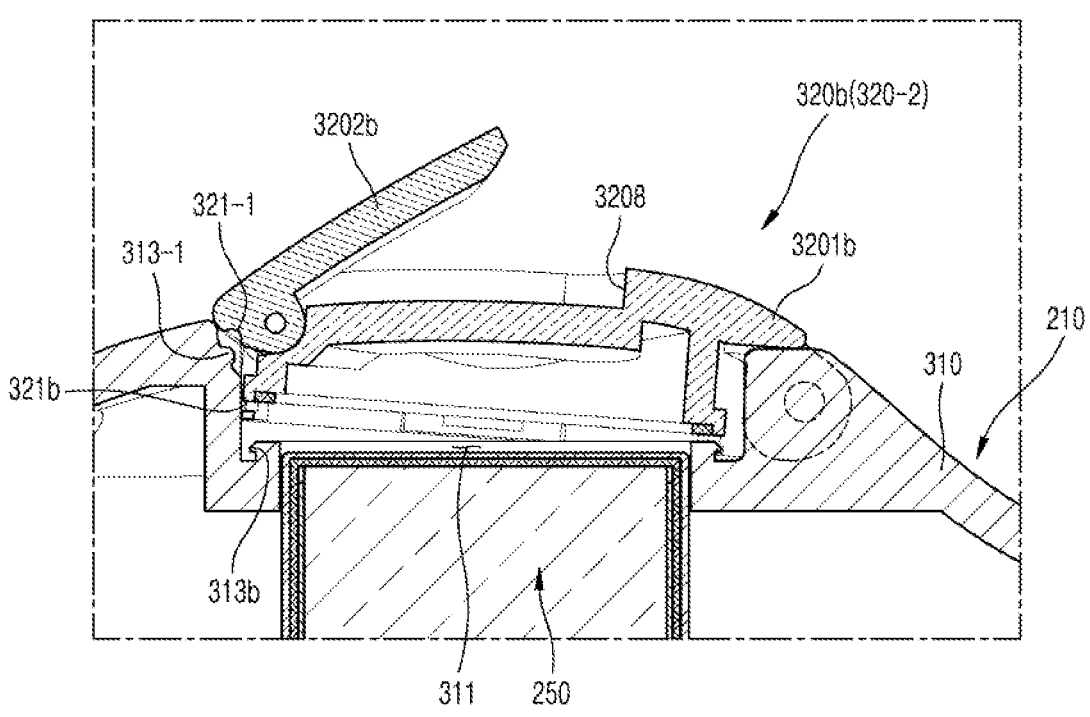
FIG. 19 is a cross-sectional view illustrating a state where a locked state is released by a locking member of the housing cap of FIG. 18.

Referring to FIGS. 18 and 19, the wireless probe 20 according to another embodiment may include a housing cap 320b configured to close the opening 311 of the outer housing 310.

The housing cap 320b may include a body 3201b that is rotatable with respect to the outer housing 310 and a cover member 3202b that is rotatable with respect to the body 3201b.

The body 3201b may include a locking member 321b configured so that the housing cap 320b is maintained at the closed position 320-2. The locking member 321b may have a groove structure into which a first locking protrusion 313b of the housing 210 may be inserted.

The cover member 3202b may include a second locking member 321-1 configured so that the housing cap 320b is maintained at the closed position 320-2. The second locking member 321-1 may have a groove structure into which a second locking protrusion 313-1 of the outer housing 310 may be inserted. The cover member 3202b may be inserted into a cover groove 3208 provided in the body 3201b. A length of the cover member 3202b may be less than a length of the cover groove 3208. Accordingly, a user may easily pivot the cover member 3202b by putting his/her finger into a space between an end of the cover member 3202b and the cover groove 3208.

The user may pivot the cover member 3202b to primarily pivot the housing cap 320b so that the second locking groove 321-1 of the cover member 3202b is separated from the second locking protrusion 313-1 of the housing 210. Next, the user may hold the cover member 3202b and secondarily pivot the housing cap 320b to open the opening 311 of the housing 210.

Due to the cover member 3202b, the user may easily release a locked state by the locking member 321. The cover member 3202b may function as a manipulation member.

In the above embodiments, the housing caps 320, 320a, and 320b may pivot with respect to the outer housing 310. However, operations of the housing caps 320, 320a, and 320b are not limited thereto, and the housing caps 320, 320a, and 320b may be detachably assembled without pivoting with respect to the housing 210.

Figure 20:
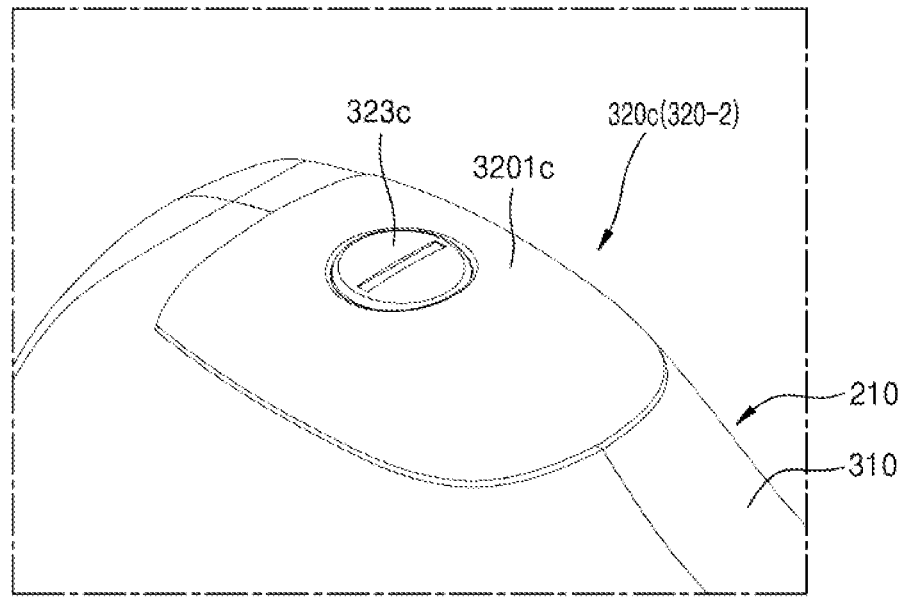
FIG. 20 is a view illustrating another example of a housing cap in a wireless probe, according to an embodiment.
Figure 21:
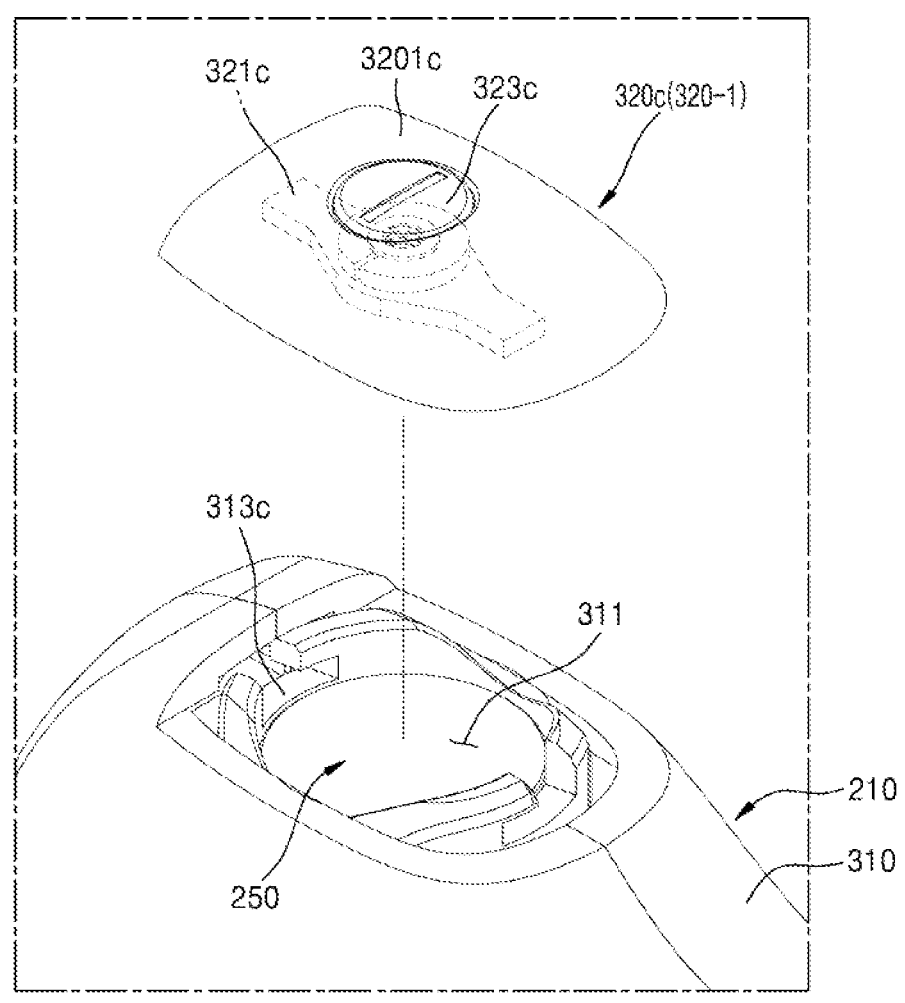
FIG. 21 is a view for describing a state where the housing cap of FIG. 20 is separated from a housing.
Figure 22:
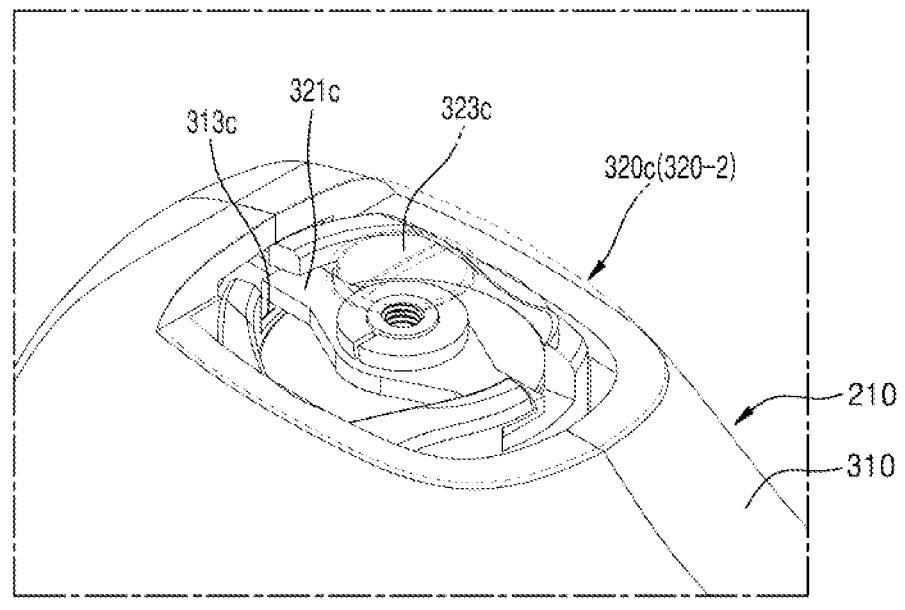
FIG. 22 is a view for describing an operation of the housing cap of FIG. 20.

Referring to FIGS. 20 to 22, a housing cap 320c according to an embodiment may be detachably assembled to the outer housing 310.

The housing cap 320c may include a locking member 321c that is pivotable in a direction intersecting a separation direction. The locking member 321c may rotate about a rotation shaft located along a direction parallel to the separation direction. The locking member 321c may be connected to a manipulation member 323c exposed to the outside of a body 3201c. Accordingly, when the manipulation member 323c is rotated, the locking member 321c located under the body 3201c may be rotated.

A locking groove 313c into which an end of the locking member 321c may be inserted in the separation direction and through which an end of the inserted locking member 321c may move in a radial direction may be provided in the outer housing 310.

A user may mount the housing cap 320c on the outer housing 310 so that an end of the locking member 321c is inserted into the locking groove 313c, and may rotate the manipulation member 323c to move the manipulation member 323c in the radial direction so that the end of the locking member 321c is caught by the locking groove 313c. Accordingly, the housing cap 320c may be mounted on the outer housing 310. The user may separate the housing cap 320c from the housing 210 in reverse order to the order in which the housing cap 320c is mounted.

Figure 23A:
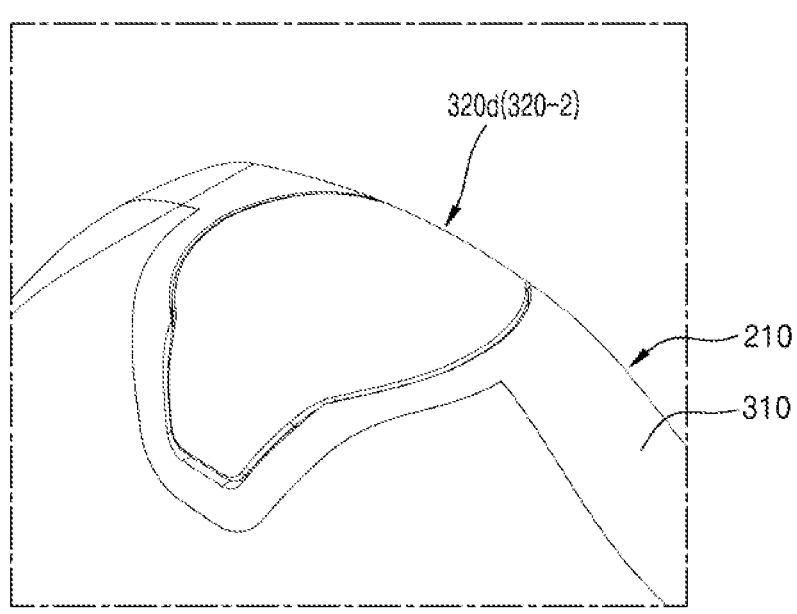
FIG. 23A is a perspective view illustrating another example of a housing cap in a wireless probe, according to an embodiment.
Figure 23B:
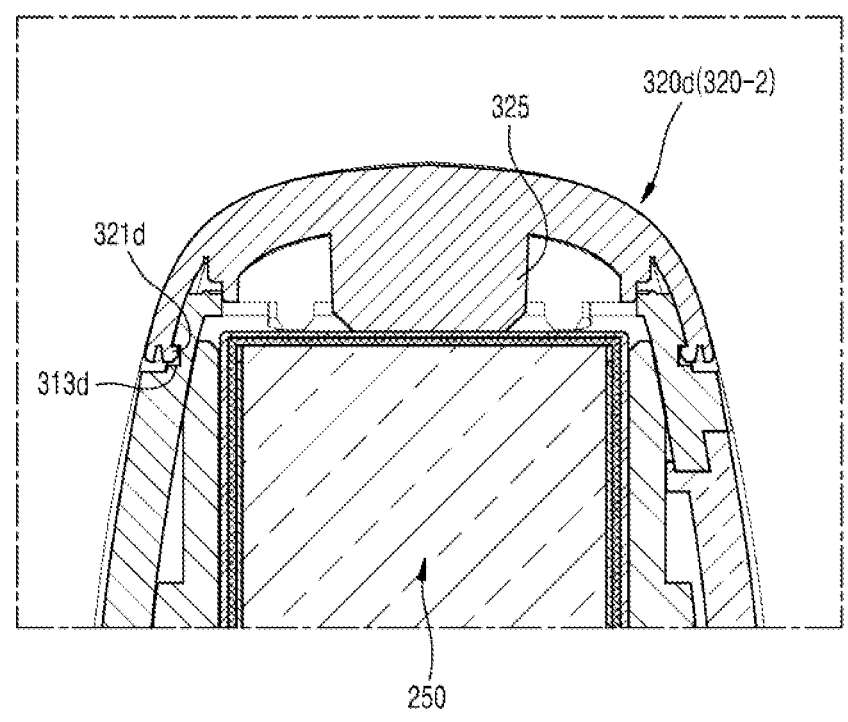
FIG. 23B is a cross-sectional view illustrating the wireless probe of FIG. 23A.
Figure 24:
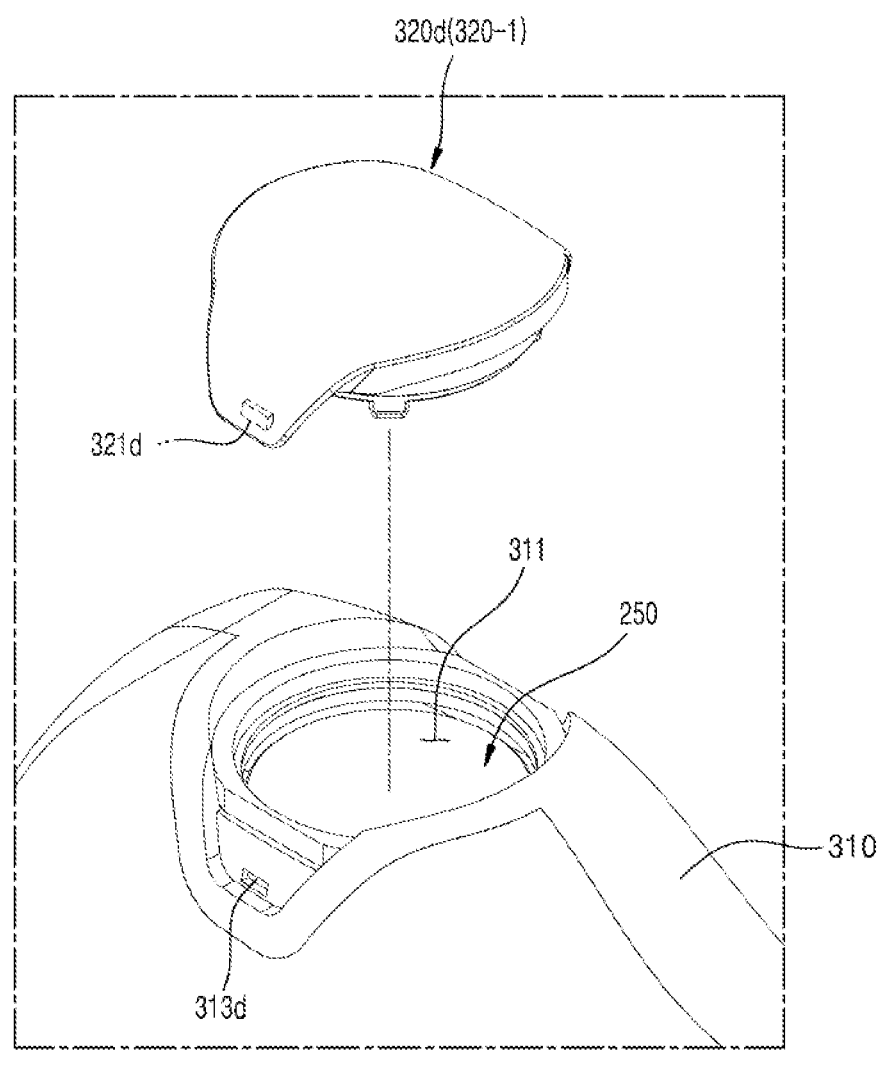
FIG. 24 is a perspective view illustrating a state where a housing cap is separated from a housing in FIG. 23A.

However, a structure in which the housing cap 320c is detachably mounted on the outer housing 310 is not limited thereto, and may vary. Referring to FIGS. 23A, 23B, and 24, a housing cap 320d according to an embodiment may be detachably assembled to the housing 210. For example, the housing cap 320d may include a locking member 321d configured so that the outer housing 310 and the housing cap 320d are fixed by hook coupling. For example, the locking member 321d may include a plurality of locking protrusions. A plurality of locking grooves 313d into which the plurality of locking protrusions may be respectively inserted may be provided in the outer housing 310.

The housing cap 320d may further include a battery pressing portion 325 configured to press the battery 250. When the housing cap 320d is mounted on the outer housing 310, the battery pressing portion 325 may press the other end of the battery 250. Accordingly, the stability of electrical connection of the battery 250 may be ensured.

Figure 25A:
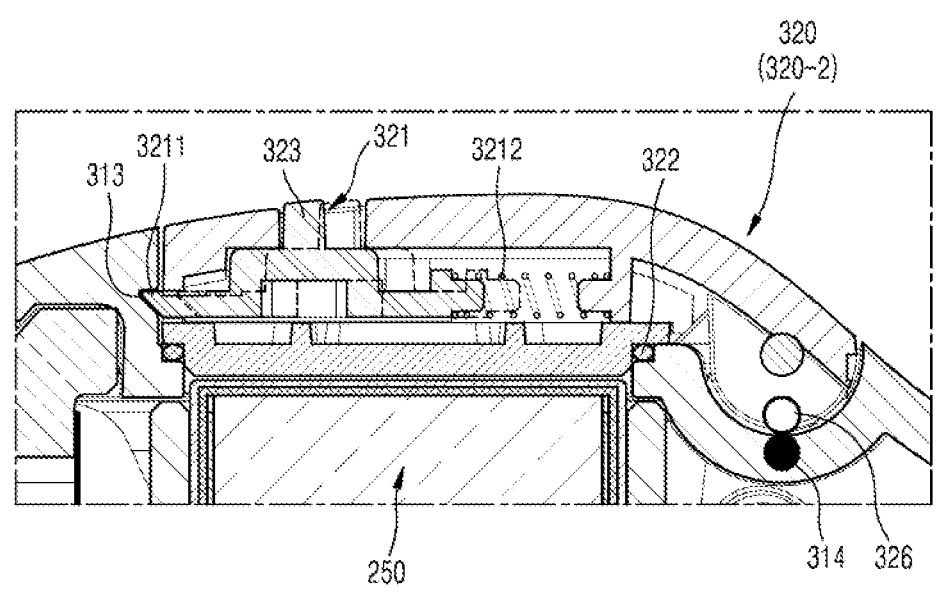
FIG. 25A is a cross-sectional view illustrating a housing cap of a wireless probe, according to an embodiment.
Figure 25B:
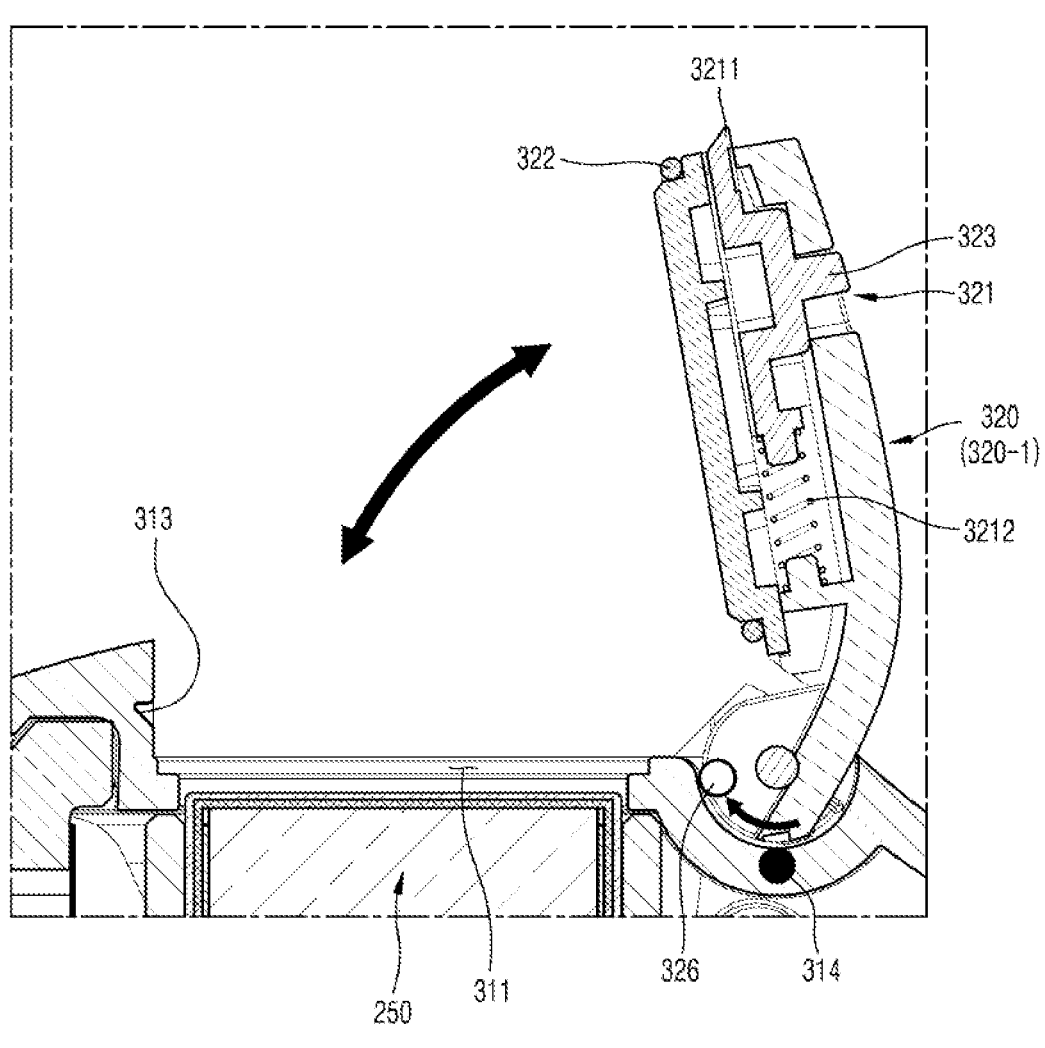
FIG. 25B is a cross-sectional view illustrating the housing cap of FIG. 25A in an open state.

FIG. 25A is a cross-sectional view illustrating the housing cap 320 of the wireless probe 20, according to an embodiment. FIG. 25B is a cross-sectional view illustrating the housing cap 320 of FIG. 25A in an open state.

Referring to FIGS. 25A and 25B, the wireless probe 20 according to an embodiment may further include a sensor 314 for detecting whether the housing cap 320 is open. For example, the sensor 314 may be located adjacent to a pivoting shaft of the housing cap 320. For example, the sensor 314 may be configured to detect a member 326 provided on the housing cap 320. For example, when the member 326 provided on the housing cap 320 is a magnet, the sensor 314 may be a sensor for detecting an intensity of a magnetic field.

However, a type and an arrangement of the sensor 314 are not limited thereto, and may vary. For example, the sensor 314 may be a contact sensor whose contact state varies according to whether the housing cap 320 is open.

Whether the first transducer 211 of the wireless probe 20 operates may vary according to information detected by the sensor 314. For example, when the open position 320-1 of the housing cap 320 is detected by the sensor 314, an operation of the first transducer 211 may be stopped. When the closed position 320-2 of the housing cap 320 is detected by the sensor 314, the first transducer 211 may operate. Accordingly, the first transducer 211 may be prevented from operating in a state where the housing cap 320 is open.

Figure 26:
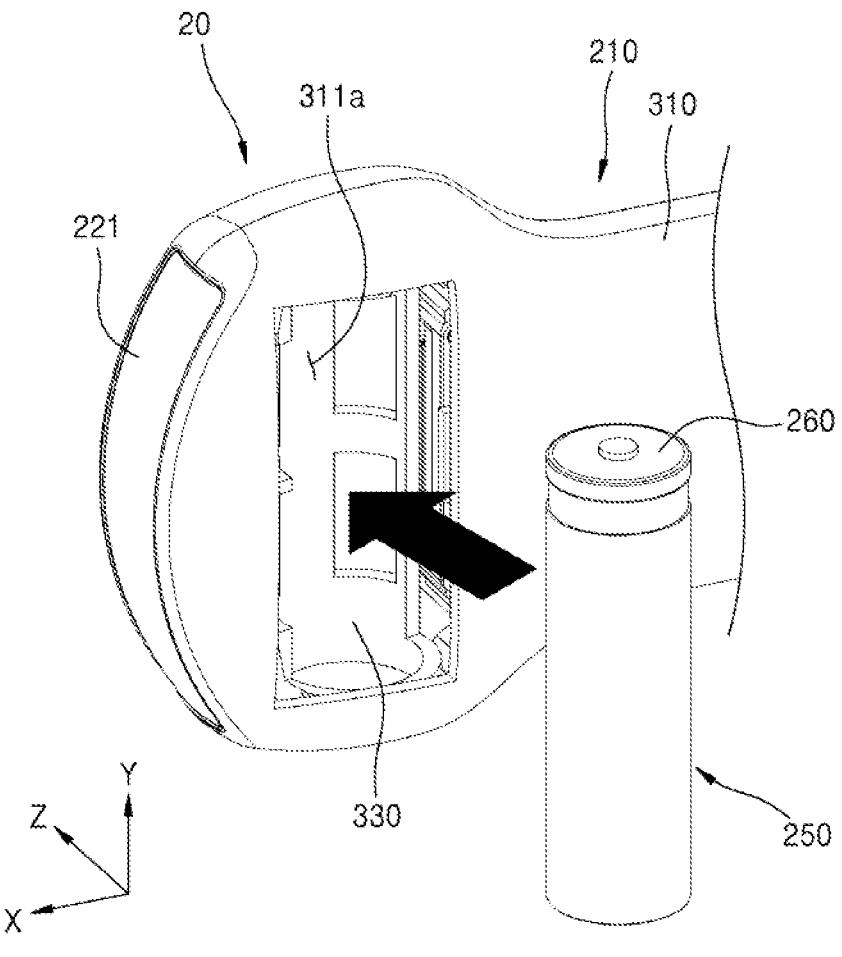
FIG. 26 is a perspective view illustrating another example of a wireless probe, according to an embodiment.

In the above embodiments, a structure in which the battery 250 may be inserted into and separated from the housing 210 along the second direction Y has been described. However, a structure of inserting and separating the battery 250 into and from the wireless probe 20 according to an embodiment is not limited thereto. For example, as shown in FIG. 26, the outer housing 310 of the wireless probe 20 may include an opening 311a through which the battery 250 may be inserted and separated into the battery accommodating unit 330 along the third direction Z.

Figure 27:
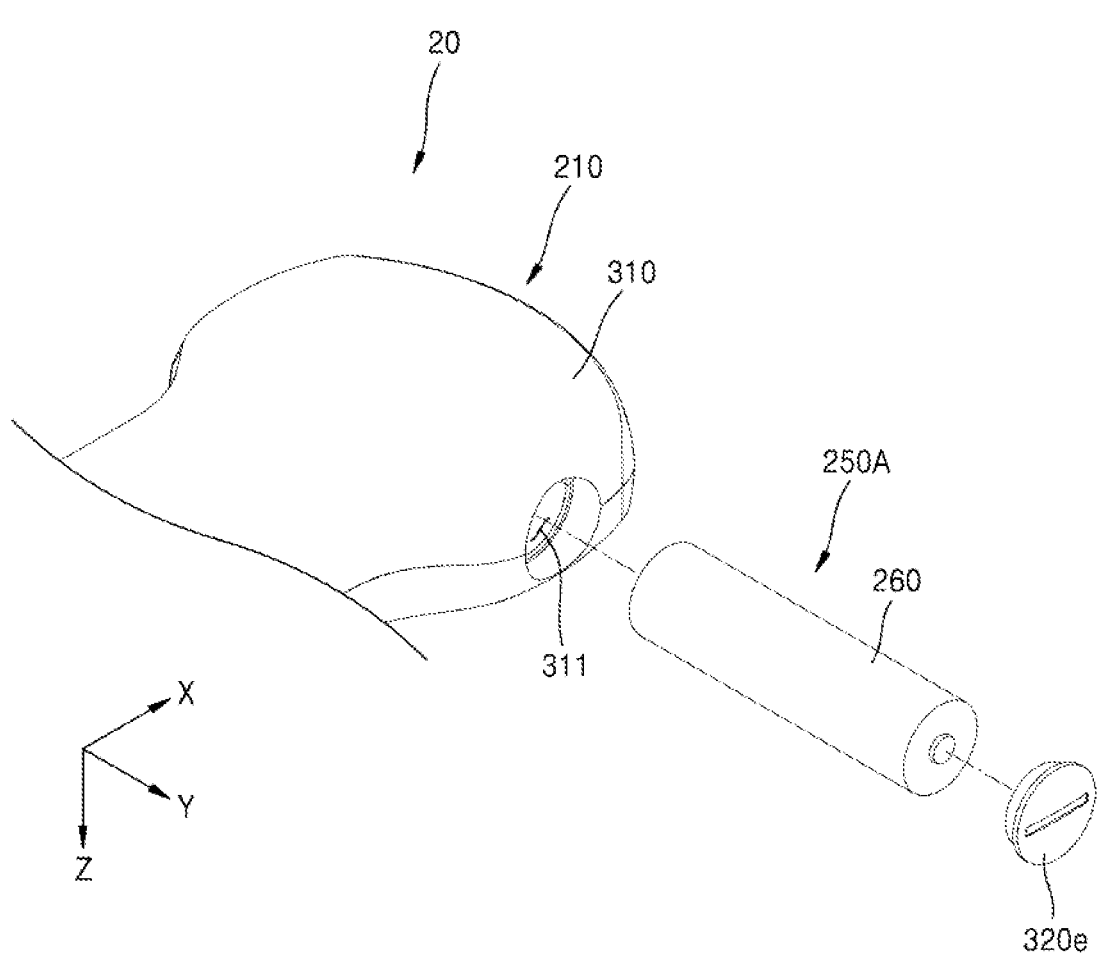
FIG. 27 is a perspective view illustrating another example of a wireless probe, according to an embodiment.

Although the battery 250 includes the battery body 260 and the electrode adjusting assembly 270 in the above embodiments, the disclosure is not limited thereto. For example, a battery 250A may include the battery body 260, without the electrode adjusting assembly 270, as shown in FIG. 27. When the battery 250A includes the battery body 260, an electrode terminal for electrical connection with the battery body 260 may be located on a housing cap 320e.

Figure 28:
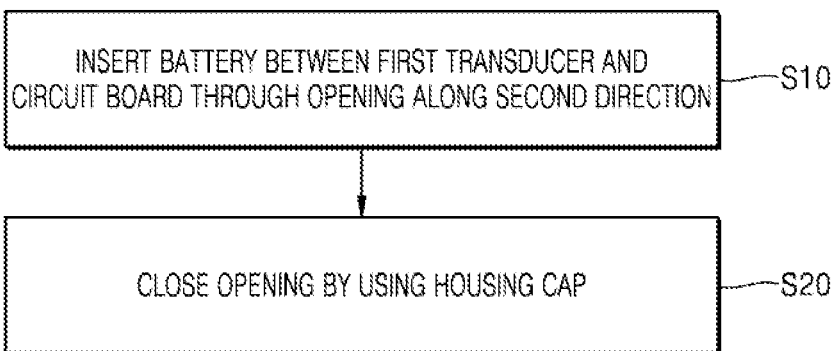
FIG. 28 is a diagram for describing a method of mounting a battery in a wireless probe, according to an embodiment.

FIG. 28 is a diagram for describing a method of mounting the battery 250 in the wireless probe 20, according to an embodiment.

Referring to FIG. 28, a method of mounting the battery 250 of the wireless probe 20 according to an embodiment may include operation S10 of inserting the battery 250 between the first transducer 221 and the circuit board 230 through the opening 311 of the outer housing 310 along a direction parallel to a longitudinal direction of the battery 250 and operation S20 of closing the opening 311 of the outer housing 310 by using the housing cap 320.

The inserting of the battery 250 may include inserting the first electrode portion 251 and the second electrode portion 2723 of the battery 250 into the opening 311 and electrically connecting the first electrode portion 251 and the second electrode portion 2723 of the battery 250 to the first electrode terminal 341 and the second electrode terminal 342.

In the wireless probe 20 according to an embodiment, an operation of the first transducer 211 may be controlled through the sensor 314. For example, even when the first electrode portion 251 and the second electrode portion 2723 are connected to the first electrode terminal 341 and the second electrode terminal 342, an operation of the first transducer 211 may be stopped before the opening 311 of the housing cap 320 is closed.

In an example, the closing of the opening 311 of the outer housing 310 may include pivoting the housing cap 320 to switch the housing cap 320 from the open position 320-1 to the closed position 320-2. After the housing cap 320 is switched to the closed position 320-2, the housing cap 320 may be maintained at the closed position 320-2 by the locking member 321.

In another example, the closing of the opening 311 of the outer housing 310 may include pivoting the housing cap 320 to which the housing cap 320 from the open position 320-1 to the closed position 320-2. After the housing cap 320 is switched to the closed position 320-2, the housing cap 320 may be maintained at the closed position 320-2 by the locking member 321.

The housing cap 320 may be assembled to the outer housing 310 by using the locking member 321 to switch the housing cap 320 from the open position 320-1 to the closed position 320-2. After the housing cap 320 is switched to the closed position 320-2, the housing cap 320 may be maintained at the closed position 320-2 by the locking member 321.

According to an embodiment, a wireless probe from and into which a battery may be separated and assembled to be located between a transducer and a circuit board may be provided.

According to an embodiment, a wireless probe in which a battery is easily separated and assembled by inserting the battery into a housing along a longitudinal direction of the battery and waterproof performance is improved may be provided.

It should be understood that embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by one of ordinary skill in the art that various changes in form and details may be made therein without departing from the spirit and scope of the disclosure as defined by the following claims.

What is claimed is:

1. A wireless probe comprising:
   a housing having a length in a first direction;
   a first transducer located at one end of the housing in the first direction;
   a circuit board located inside the housing and spaced apart from the first transducer along the first direction;
   a battery, having a largest dimension measured along a second direction perpendicular to the first direction, located between the first transducer and the circuit board in the first direction inside the housing; and
   at least one flexible circuit unit configured to electrically connect the circuit board to the first transducer,
   wherein the housing is configured to allow the battery to be inserted and separated along the second direction,
   wherein the housing comprises:
   an outer housing forming an exterior and comprising an opening formed at one end in the second direction;
   a housing cap forming an exterior and configured to open and close the opening; and
   a battery accommodating unit located inside the outer housing and configured to accommodate the battery inserted in the second direction through the opening therein,
   wherein the at least one flexible circuit unit is configured to surround a side portion of the battery accommodating unit to bypass the battery accommodating unit,
   wherein the battery accommodating unit is configured to prevent contact between the at least one flexible circuit unit and the battery while the battery is inserted into or separated from the battery accommodating unit along the second direction.

2. The wireless probe of claim 1, wherein the battery accommodating unit is connected to the opening, has a cross-sectional shape corresponding to a cross-sectional shape of the battery, and extends along the second direction.

3. The wireless probe of claim 1, wherein the battery comprises a first electrode portion and a second electrode portion located adjacent to each other at the front in an insertion direction.

4. The wireless probe of claim 3, wherein the battery comprises a battery body comprising a first electrode and a second electrode having different polarities and provided at both ends in a longitudinal direction, and an electrode adjusting assembly exposing the first electrode to outside to form the first electrode portion, covering the second electrode, and electrically connected to the second electrode to form the second electrode portion adjacent to the first electrode portion.

5. The wireless probe of claim 4, wherein the electrode adjusting assembly comprises an inner insulator configured to surround an outer surface of the battery body and expose the first electrode and the second electrode through both ends of the inner insulator, an electrode moving body comprising an electrode contact portion contacting the second electrode exposed through the inner insulator, the second electrode portion located at a position spaced apart from the electrode contact portion, and an extending portion electrically connecting the electrode contact portion to the second electrode portion, and an outer insulator configured to surround an outer surface of the inner insulator, cover the electrode contact portion and the extending portion of the electrode moving body, and expose the second electrode portion.

6. The wireless probe of claim 5, further comprising a sealing member located on at least one of the outer housing and the housing cap to prevent penetration of water between the outer housing and the housing cap.

7. The wireless probe of claim 5, further comprising a sensor configured to detect whether the housing cap is at an open position, wherein an operation of the first transducer is controlled based on a detection result of the sensor.

8. The wireless probe of claim 6, wherein the battery accommodating unit comprises a first electrode terminal for electrical contact with the first electrode portion of the battery, and a second electrode terminal for electrical contact with the second electrode portion of the battery, wherein directions of the first electrode terminal and the second electrode terminal are perpendicular to each other.

9. The wireless probe of claim 8, wherein an outer diameter of the second electrode portion is less than an outer diameter of the outer insulator so that the second electrode portion forms a concave portion of the battery.

10. The wireless probe of claim 6, wherein, when the battery is inserted into the battery accommodating unit, a distance between the second electrode portion of the battery and the opening along the second direction is greater than a distance between the second electrode of the battery body and the opening along the second direction.

11. The wireless probe of claim 1, wherein a difference between a length of the first transducer along the second direction and a length of the battery along the second direction is 20% or less of the length of the battery along the second direction.

12. The wireless probe of claim 1, wherein the housing cap has an open position for opening the opening and a closed position for closing the opening, wherein the housing cap comprises a locking member configured to maintain the closed position.

13. The wireless probe of claim 12, further comprising a manipulation member configured to facilitate release of a locked state by the locking member.

14. The wireless probe of claim 1, further comprising a second transducer located at the other end of the housing, wherein a width of the first transducer in the second direction is different from a width of the second transducer in the second direction.

15. The wireless probe of claim 1, wherein the housing cap is attached to the one end of the outer housing in the second direction, such that the battery is inserted into or separated from the battery accommodating unit along the second direction.

* * * * *